(12) United States Patent
Karasawa

(10) Patent No.: US 7,713,206 B2
(45) Date of Patent: May 11, 2010

(54) ULTRASONIC IMAGING APPARATUS

(75) Inventor: Hiroyuki Karasawa, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 1260 days.

(21) Appl. No.: 11/234,088

(22) Filed: Sep. 26, 2005

(65) Prior Publication Data

US 2006/0079776 A1    Apr. 13, 2006

(30) Foreign Application Priority Data

Sep. 29, 2004   (JP)  ............................. 2004-283319

(51) Int. Cl.
*A61B 8/00* (2006.01)
(52) U.S. Cl. .................. 600/443; 600/437; 600/441
(58) Field of Classification Search ............... 600/437, 600/443, 441
See application file for complete search history.

(56) References Cited

U.S. PATENT DOCUMENTS 6,398,733 B1 *   6/2002   Simopoulos et al.   ......... 600/443

2003/0092993 A1 *   5/2003   Grunwald   .................. 600/462
2005/0075565 A1 *   4/2005   Satoh   ........................ 600/437

FOREIGN PATENT DOCUMENTS

| JP | 08-117225 A | 5/1996 |
|---|---|---|
| JP | 10-258052 A | 9/1998 |
| JP | 11-235341 A | 8/1999 |
| JP | 2003-061964 A | 3/2003 |
| WO | WO 00/40997 A1 | 7/2000 |

* cited by examiner

*Primary Examiner*—Brian Casler
*Assistant Examiner*—John F Ramirez
(74) *Attorney, Agent, or Firm*—Sughrue Mion, PLLC

(57) ABSTRACT

Tissue property of a reflector is detected based on plural reception signals outputted from plural ultrasonic transducers by receiving ultrasonic echoes. An ultrasonic imaging apparatus includes: an ultrasonic probe including plural ultrasonic transducers for transmitting ultrasonic waves toward an object to be inspected and receiving ultrasonic waves reflected from the object to output plural reception signals; and a tissue property image generating unit for generating information on tissue property in a region within the object based on interrelationship among at least one group of reception signals on the region from among the plural reception signals respectively outputted from the plural ultrasonic transducers.

10 Claims, 20 Drawing Sheets

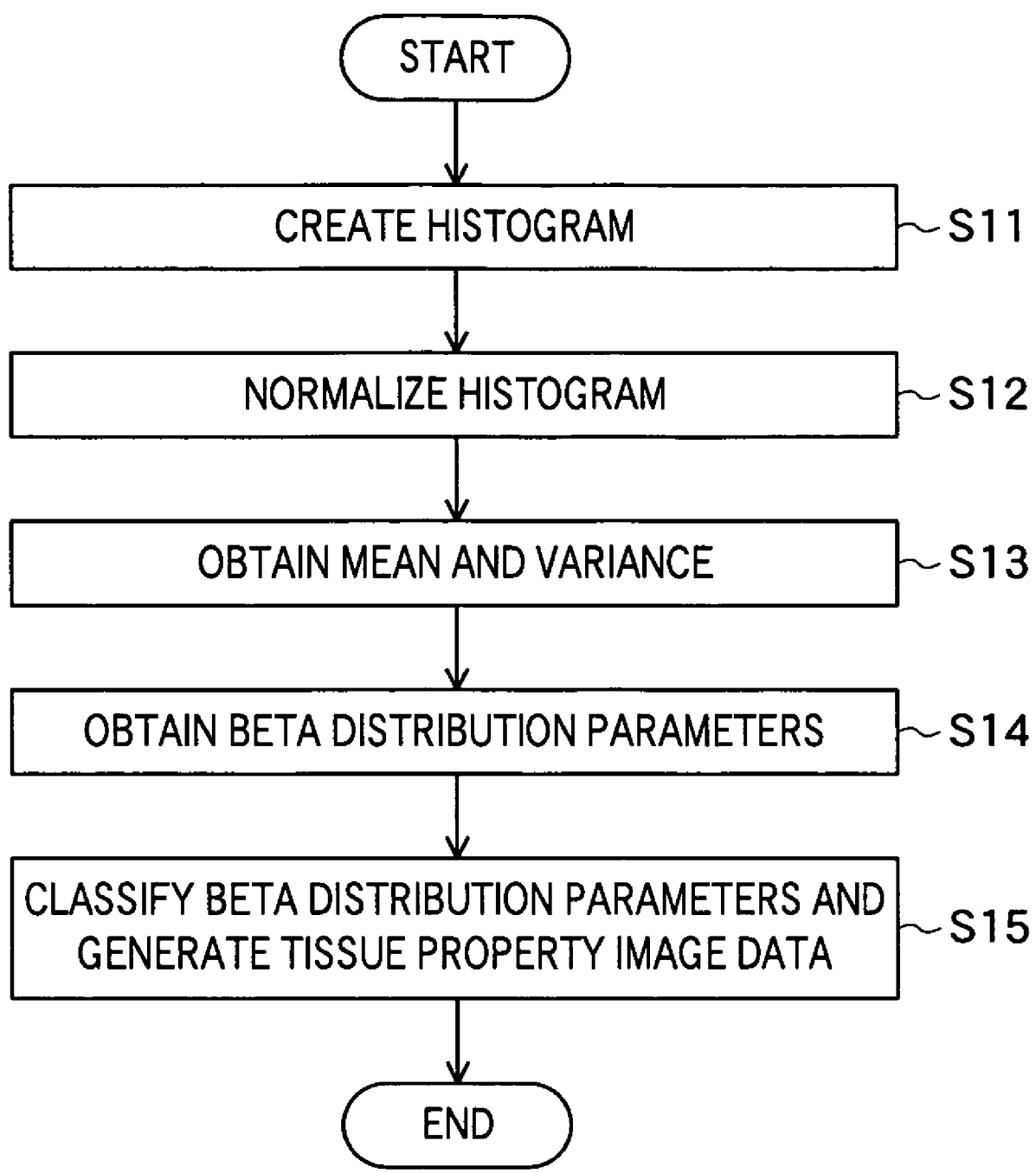

FIG.13

| | $\beta < 1$ | $\beta = 1$ | $1 < \beta < 2$ | $\beta = 2$ | $\beta > 2$ |
|---|---|---|---|---|---|
| $\alpha < 1$ | U-SHAPED | J-SHAPED | J-SHAPED | J-SHAPED | J-SHAPED |
| $\alpha = 1$ | J-SHAPED | UNIFORM | J-SHAPED | J-SHAPED (STRAIGHT LINE) | J-SHAPED |
| $1 < \alpha < 2$ | J-SHAPED | J-SHAPED | SINGLE-PEAKED | SINGLE-PEAKED | SINGLE-PEAKED |
| $\alpha = 2$ | J-SHAPED | J-SHAPED (STRAIGHT LINE) | SINGLE-PEAKED | SINGLE-PEAKED | SINGLE-PEAKED |
| $\alpha > 2$ | J-SHAPED | J-SHAPED | SINGLE-PEAKED | SINGLE-PEAKED | SINGLE-PEAKED |

ULTRASONIC IMAGING APPARATUS

BACKGROUND OF THE INVENTION

1. Field of the Invention

The present invention relates to an ultrasonic imaging apparatus for transmitting and receiving ultrasonic waves to perform imaging of organs, bones, etc. within a living body thereby generating ultrasonic images to be used for diagnosis.

2. Description of a Related Art

In an ultrasonic imaging apparatus to be used for medical diagnoses, an ultrasonic probe including plural ultrasonic transducers having transmitting and receiving functions of ultrasonic waves is used. When an ultrasonic beam formed by synthesizing plural ultrasonic waves is transmitted from such an ultrasonic probe to an object to be inspected, the ultrasonic beam is reflected at a boundary between regions having different acoustic impedances, i.e., between tissues within the object. Thus generated ultrasonic echoes are received and an image is constructed based on the intensity of the ultrasonic echoes, and thereby, the state within the object can be reproduced on a screen.

As described above, a general ultrasonic image represents a shape of a tissue within the object by utilizing the difference in acoustic impedance between tissues. Accordingly, in an ultrasonic image of an organ like a liver which is formed by a number of reflectors nearly in size of the wavelength of ultrasonic waves, speckle pattern components, in which light points and dark points are scattered, mainly appear due to interference between ultrasonic echoes. In such an ultrasonic image, even when a tumor or the like is included in a tissue within the organ, no distinct reflection surface is seen at the outline of the tissue, and therefore, the difference between a normal tissue and an abnormal tissue can be determined only by the difference between speckle patterns. Accordingly, determination of tissue property of the tumor or the like and medical diagnoses based thereon are difficult. Further, with respect to a region like the vicinity of the bone part where soft tissues such as muscles and hard tissues such as bones, tendons, and nucleus pulposus are intricate, it is also extremely difficult to visually recognize the soft tissues from the hard tissues. Therefore, when an ultrasonic image is generated, the use of elements other than intensity of ultrasonic echoes has been studied. As the elements, it is conceivable to utilize statistical property (statistics values) representing interrelationships among plural ultrasonic echo signals respectively received by plural ultrasonic transducers.

As a related technology, International Publication WO00/40997 discloses that the obtained echo signals are processed along both processing paths of one reception signal processing path using time delays set for a traditional coherent receive beam forming and another reception signal processing path using time delays set to apply incoherent summing using time delays equal to, for example, zero and an ultrasonic image is generated based on thus obtained coherent summation signals and incoherent summation signals in order to prevent incoherent summation of phase matching signals due to variations in propagation times and image deterioration in an ultrasonic image by suppressing a display based on incoherent summation signals (page 1). Further, in WO00/40997, an image is generated based on a coherence factor, and displayed as a color map overlaid on a B-mode image. Here, the coherence factor refers to the degree of similarity of a signal that has been phase matched (coherent summed signal A) and a signal that has not been phase matched (incoherent summed signal B), and expressed by the difference between the signal A and signal B, the ratio of the signal A to the signal B, or the like.

According to WO00/40997, it can be expected that the image quality of an ultrasonic image may be improved by making a choice among reception signals based on the coherence factor. However, a tissue property or the angle relative to an ultrasonic beam of a reflector is not obtained. Further, any analysis of signals before phase matching (i.e., plural reception signals that form the above-mentioned signal A or signal B) is not performed.

Further, Japanese Patent Application Publication JP-A-11-235341 discloses an ultrasonic diagnostic apparatus for providing directional characteristics of transmission and reception by providing individual delay times to excitation signals of respective arranged plural vibrators and reception signals obtained by these vibrators by receiving ultrasonic reflection waves from an object to be inspected and obtaining an ultrasonic image by scanning within the object with the ultrasonic waves provided with directional characteristics in order to suppress influence of the distortion on image quality even when waveforms of reception signals are distorted due to refraction, multiple reflection, or the like (page 1). The ultrasonic diagnostic apparatus includes a reception signal evaluation unit for evaluating the distortion of the reception signals with respect to each vibrator and an aperture control unit for controlling at least one of intensity of the excitation signals and amplification factor of the reception signals based on a result of the evaluation, wherein the degree of distortion is evaluated by utilizing waveform similarity, correlation coefficients, intensity, or the like of the plural reception signals.

According to JP-A-11-235341, it can be expected that the image quality of an ultrasonic image may be improved by using the waveform distortion of the reception signals as a parameter. However, also in JP-A-11-235341, a tissue property or the angle relative of a reflector to an ultrasonic beam is not obtained. Further, the intensity of reception signals is used for waveform similarity, but various kinds of statistical property are not utilized.

JP-A-10-258052 discloses a wave receiving apparatus including a receiver for detecting orientation or displacement of a target of detection by one reception with a predetermined aperture in an arbitrary position and receiving wave that has reached within the aperture with information on a position within the aperture in order to obtain high resolving power or obtain signals equivalent of reception signals corresponding to an aperture that actually receives no signal, a weighting processing unit for weighting the signals obtained by the receiver by using respective kinds of weighting functions having variables corresponding to the position within the aperture, and a computing unit for performing a computation including a computation for obtaining a propagation direction of the wave that has reached the aperture or a position of a wave source that has generated the wave based on plural weighted reception signals obtained by weighting processing by the weighting processing unit (page 1).

According to JP-A-10-258052, the orientation and position of the target of detection can be detected by weighting the reception signals according to the position within the aperture. However, mutual property and statistics values of reception signals obtained from plural ultrasonic transducers are not utilized, and a tissue property of a target object cannot be identified.

JP-A-8-117225 discloses a living tissue evaluation apparatus including transmitting means for transmitting ultrasonic waves to a living tissue, intensity distribution obtaining means for obtaining an intensity distribution of ultrasonic waves by receiving ultrasonic waves that have been transmitted through the living tissue and spread, and evaluation value computing means for calculating an evaluation value of the living tissue based on the obtained intensity distribution for analyzing a microscopic structure of the living body by utilizing information on spatial spreading of ultrasonic waves transmitted through the living tissue (page 1).

According to JP-A-8-117225, the intensity distribution among ultrasonic vibrators is obtained. However, since an interference phenomenon in transmission is used, information on the depth by the ultrasonic beam cannot be obtained and property within the tissue is obtained only as integration information. Further, any information within objects can be obtained except for an object within which ultrasonic interference occurs.

Further, JP-P2003-61964A discloses an ultrasonic diagnostic apparatus for applying ultrasonic pulses to an object to be inspected to obtain a tomographic image, smoothing the image by utilizing statistical property of a speckle pattern, and extracting a microstructure in order to observe a minute abnormal lesion within a homogeneous tissue structure (page 2). The ultrasonic diagnostic apparatus includes analysis computation means for extracting a specific signal by using intensity or statistical property of amplitude information of echo signals generated from a part of the object, and display means for displaying a result extracted from the analysis computation means.

According to JP-P2003-61964A, the intensity statistics value of a signal after phase matching is imaged, however, any element-level signal is not referred to.

Thus, according to the above documents, the image quality improvement in ultrasonic image may be expected, however, tissue property of a reflector cannot be obtained.

SUMMARY OF THE INVENTION

The present invention has been achieved in view of the above-mentioned problems. A first object of the present invention is to detect tissue property of a reflector based on plural reception signals respectively outputted from plural ultrasonic transducers by receiving ultrasonic echoes. Further, a second object of the present invention is to understandably demonstrate tissue property of a reflector by separating ultrasonic echo signals representing the tissues of the reflector and ultrasonic echo signals representing speckle components. Furthermore, a third object of the present invention is to perform image display suitable for medical diagnoses by clearly and distinctively showing soft tissues and hard tissues.

In order to solve the above-mentioned problems, an ultrasonic imaging apparatus according to one aspect of the present invention includes: an ultrasonic probe including plural ultrasonic transducers for by transmitting ultrasonic waves toward an object to be inspected and receiving ultrasonic waves reflected from the object to output reception signals; and tissue property information generating means for generating information on tissue property in a region within the object based on interrelationship among at least one group of reception signals on the region from among the plural reception signals respectively outputted from the plural ultrasonic transducers.

According to the present invention, information on tissue property within the object can be obtained by utilizing amounts representing the interrelationship among plural reception signals as a parameter. Therefore, the quality and efficiency of medical diagnoses using ultrasonic images can be improved by imaging the difference of thus obtained property among tissues and utilizing it besides shapes of tissues within the object shown by a B-mode image.

BRIEF DESCRIPTION OF THE DRAWINGS

FIG. 11 is a flowchart showing an operation of a histogram analysis unit and a tissue property image data generating unit according to a first example;

FIG. 13 is a chart showing classified parameters of a beta distribution;

DESCRIPTION OF THE PREFERRED EMBODIMENTS

Figure 1:
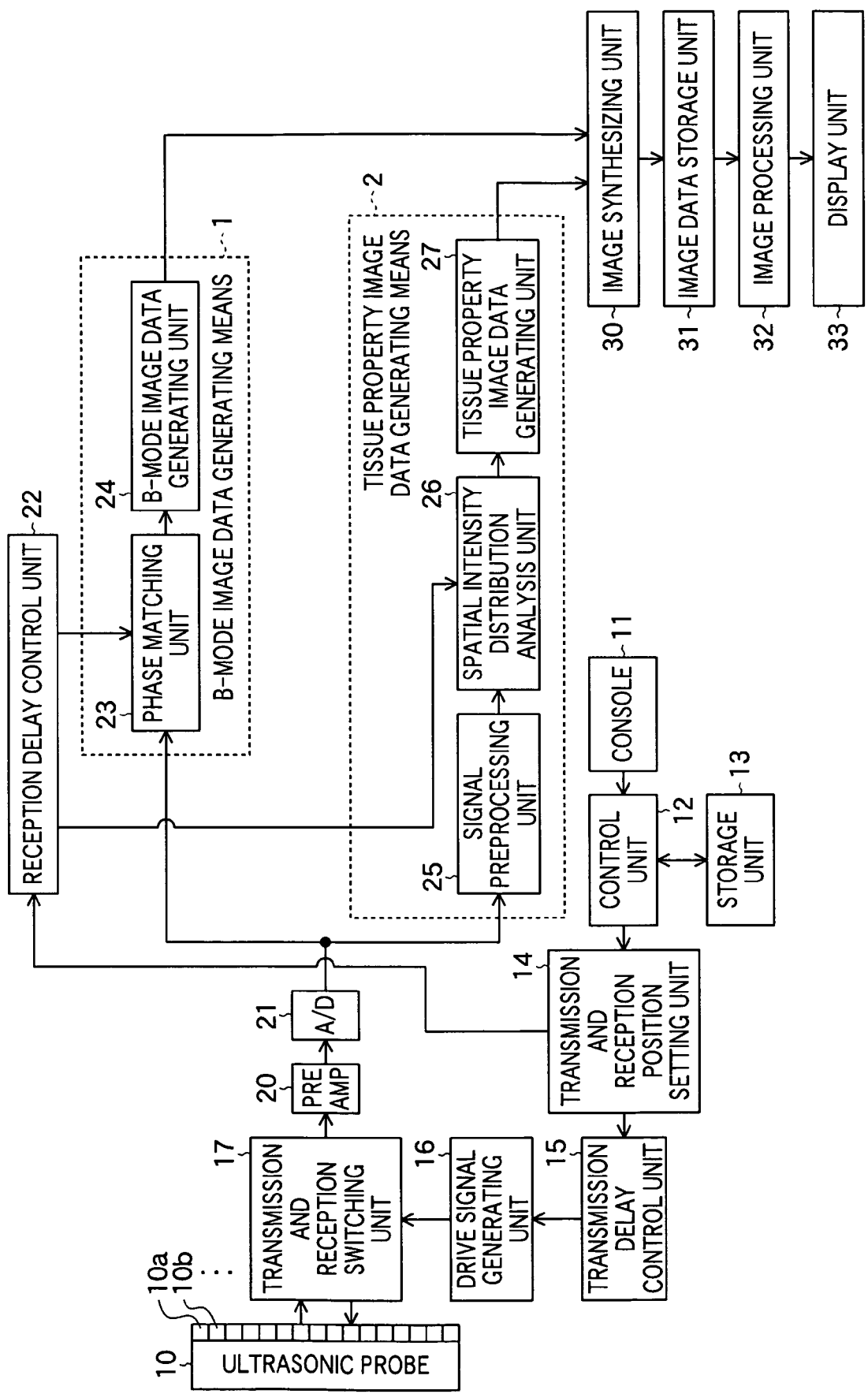
FIG. 1 is a block diagram showing a constitution of an ultrasonic imaging apparatus according to the first embodiment of the present invention.

Hereinafter, preferred embodiments of the present invention will be described in detail by referring to the drawings. The same reference numbers are assigned to the same component elements and the description thereof will be omitted.

FIG. 1 is a block diagram showing a constitution of an ultrasonic imaging apparatus according to the first embodiment of the present invention. The ultrasonic imaging apparatus according to the embodiment includes an ultrasonic probe 10, a console 11, a control unit 12, a storage unit 13, a transmission and reception position setting unit 14, a transmission delay control unit 15, a drive signal generating unit 16, and a transmission and reception switching unit 17.

The ultrasonic probe 10 is used by being abutted on an object to be inspected to transmit ultrasonic waves to the object and receive ultrasonic waves reflected from the object. The ultrasonic probe 10 includes plural ultrasonic transducers 10a, 10b, . . . for transmitting ultrasonic beams based on applied drive signals, receiving propagating ultrasonic echoes to output reception signals. These ultrasonic transducers 10a, 10b, . . . are arranged in a one-dimensional or two-dimensional manner to form a transducer array.

Each ultrasonic transducer is constituted by a vibrator in which electrodes are formed on both ends of a material having a piezoelectric property (piezoelectric material) such as a piezoelectric ceramic represented by PZT (Pb (lead) zirconate titanate), a polymeric piezoelectric material represented by PVDF (polyvinylidene difluoride), or the like. When a voltage is applied to the electrodes of the vibrator by transmitting pulse electric signals or continuous wave electric signals, the piezoelectric material expands and contracts. By the expansion and contraction, pulse ultrasonic waves or continuous wave ultrasonic waves are generated from the respective vibrators, and an ultrasonic beam is formed by synthesizing these ultrasonic waves. Further, the respective vibrators expand and contract by receiving propagating ultrasonic waves and generate electric signals. These electric signals are outputted as detection signals of ultrasonic waves.

Alternatively, as the ultrasonic transducers, plural kinds of elements of different conversion types may be used. For example, the above-mentioned vibrators are used as elements for transmitting ultrasonic waves and photo-detection type ultrasonic transducers are used as elements for receiving ultrasonic waves. The photo-detection type ultrasonic transducer is for detecting ultrasonic waves by converting ultrasonic signals into optical signals, and constituted by a Fabry-Perot resonator or fiber Bragg grating, for example.

The console 11 is used when an operator inputs commands and information to the ultrasonic imaging apparatus. The console 11 includes a keyboard, adjustment knob, and a pointing device including mouse, or the like.

The control unit 12 is formed by a CPU and software, for example, and controls the respective units of the ultrasonic imaging apparatus based on the commands and information input from the console 11. In the storage unit 13, programs for allowing the CPU that forms the control unit 12 to execute operation or the like are stored.

The transmission and reception position setting unit 14 sets the transmission direction, reception direction, and depth of focus of the ultrasonic beam transmitted from the ultrasonic probe 10 and the aperture diameter of the ultrasonic transducer array (i.e., plural ultrasonic transducers to be used) in order to scan a predetermined region within the object by the ultrasonic beam. Further, the transmission delay control unit 15 sets delay times to be provided to the plural ultrasonic transducers for transmitting the ultrasonic beam that has been set by the transmission and reception position setting unit 14.

The drive signal generating unit 16 includes plural drive circuits for generating plural drive signals to be supplied to the plural ultrasonic transducers, respectively. These drive circuits generates drive signals based on the delay times that have been set in the transmission delay control unit 15.

The transmission and reception switching unit 17 switches between a transmission mode in which drive signals are supplied to the ultrasonic probe 10 and a reception mode in which reception signals are outputted from the ultrasonic probe 10 under the control of the control unit 11.

Further, the ultrasonic imaging apparatus according to the embodiment includes a preamplifier (PREAMP) 20, an A/D converter 21, a reception delay control unit 22, B-mode image data generating means 1, tissue property image data generating means 2, an image synthesizing unit 30, an image data storage unit 31, an image processing unit 32, and a display unit 33.

The preamplifier 20 and the A/D converter 21 have plural channels corresponding to the plural ultrasonic transducers 10a, 10b, . . . , input reception signals outputted from the plural ultrasonic transducers and perform preamplification and analog/digital conversion on the respective reception signals.

The reception delay control unit 22 has plural delay patterns (phase matching patterns) corresponding to the reception direction and focal depth of the ultrasonic echoes, and selects delay patterns to be provided to the plural reception signals according to the reception direction and focal depth that have been set by the transmission and reception position setting unit 14 and supplies them to a phase matching unit 23 and a spatial intensity distribution analysis unit 26.

The B-mode image data generating means 1 includes the phase matching unit 23 and a B-mode image generating unit 24.

The phase matching unit 23 performs reception focus processing by providing delays to the plural reception signals (reception data) that have been A/D converted, respectively, based on the delay pattern that has been supplied from the reception delay control unit 22, and adding the signals. By the reception focus processing, sound ray signals (sound ray data) in which focal points of ultrasonic echoes are narrowed are formed.

The B-mode image data generating unit 24 generates B-mode image data by performing envelope detection processing and STC (sensitivity time gain control) on the sound ray data that has been formed in the phase matching unit 23.

On the other hand, the tissue property image data generating means 2 includes a signal preprocessing unit 25, the spatial intensity distribution analysis unit 26, and a tissue property image data generating unit 27.

The signal preprocessing unit 25 performs the following intensity corrections (i) to (iii) on the plural reception signals that have been A/D converted according to need.

(i) Element Sensitivity Correction

Variations in performance of ultrasonic transducers generated when an ultrasonic transducer array is manufactured are corrected. The correction can be performed in the manner in which a correction table is created in advance by transmitting and receiving ultrasonic waves from the ultrasonic probe 10 while employing a standard reflection source and measuring the characteristics of the respective ultrasonic transducers, and the correction table is used at the time of processing of reception signals.

(ii) Solid Angle Intensity Correction

In an ultrasonic transducer array, since the solid angle relative to the reflection position of the ultrasonic echo becomes smaller as an ultrasonic transducer is located closer to the end of the aperture, apparent reception intensity becomes smaller. Accordingly, intensity correction is performed on the reception signals according to the reception depth (the depth of the reflection position of the ultrasonic echoes), positional relationship with the respective ultrasonic transducers, and differences in reception solid angle between ultrasonic transducers determined by the aperture.

(iii) Distance Correction

The distance attenuation of the ultrasonic echoes that varies depending on the reception depth and positional relationship with respect to the respective ultrasonic transducers are corrected. Since the amount of correction differs depending on the part to be observed, standard values according to parts to be observed may be set as default values in advance, and the operator may change the setting value while watching the displayed image.

Further, the signal preprocessing unit 25 performs processing such as smoothing and envelope detection on the corrected reception signals and converts those reception signals into digital signals. Thus, the envelope detection processing before data analysis for tissue property image generation can suppress the influence by the noise and reduce the calculation amount in the subsequent processing. Furthermore, as described below, the generated tissue property image data can be superimposed on the B-mode image data without change.

The spatial intensity distribution analysis unit 26 performs computations of calculating various statistics values by obtaining a spatial intensity distribution (hereinafter, simply referred to as "intensity distribution") of the plural reception signals on the same phase matching line from among the plural reception signals processed in the signal preprocessing unit 25 and analyzing them. These plural reception signals on the same phase matching line are determined based on the delay pattern supplied from the reception delay control unit 22. As described below, those statistics values represent qualitative information on tissue property of reflectors. Here, the tissue property of reflectors includes not only the surface conditions (surface property) such that the reflector surface is hard (e.g., bone part, tendon, and ligament) or soft (e.g., skin and muscle) but also that the tissue is a uniform internal tissue, speckle patterns, or the like.

The tissue property image data generating unit 27 generates tissue property image data as information representing tissue property of the reflectors within the object by utilizing various statistics values calculated by the spatial intensity distribution analysis unit 26 as parameters. The tissue property image data represents color signals when an ultrasonic image is displayed on the screen, and the surface property of the reflectors and internal tissues are displayed in different colors in the tissue property image.

The principle of image generation in the tissue property image data generating means 2 will be described later in detail.

The image synthesizing unit 30 generates synthesized image data in which a tissue property image is superimposed upon corresponding regions of the B-mode image based on the B-mode image data generated in the B-mode image generating unit 24 and the tissue property image data generated in the tissue property image data generating unit 27. The region of the B-mode image upon which the tissue property image is to be superimposed may be automatically determined by the image synthesizing unit 30, or may be manually designated by the operator by using the console 11.

The image data storage unit 31 stores generated synthesized image data. Further, the image processing unit 32 generates image data for screen display by performing predetermined image processing including scan conversion, gradation processing, and the like on the synthesized image data. The display unit 33 includes a display device such as a CRT or LCD, and displays an ultrasonic image based on the image data that has been image processed in the image processing unit 32.

Next, the principle of tissue property image generation will be described.

Figure 2A:
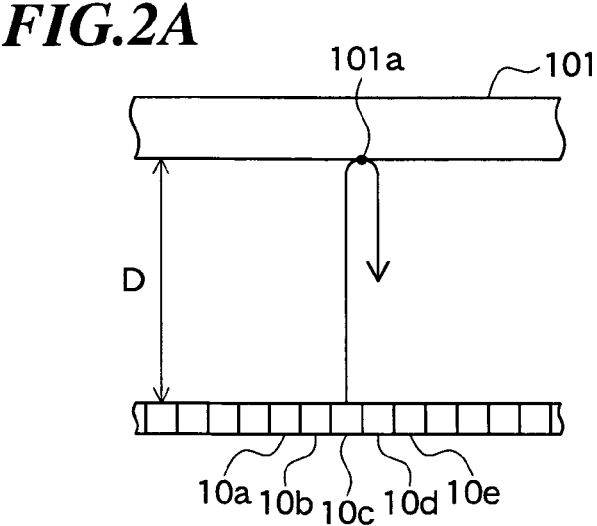
FIGS. 2A to 2C show an intensity distribution of reception signals when ultrasonic waves are transmitted toward a specular reflector and received.
Figure 2B:
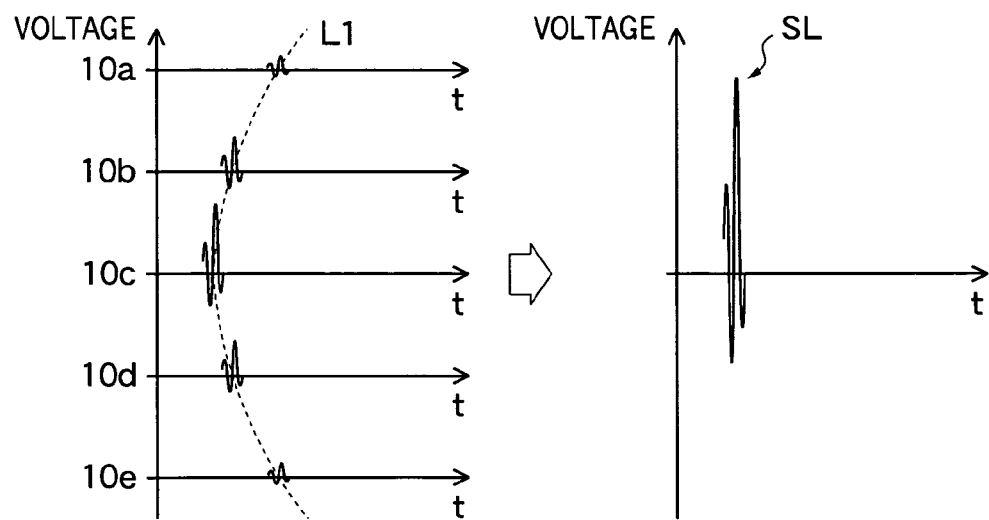
Figure 2C:
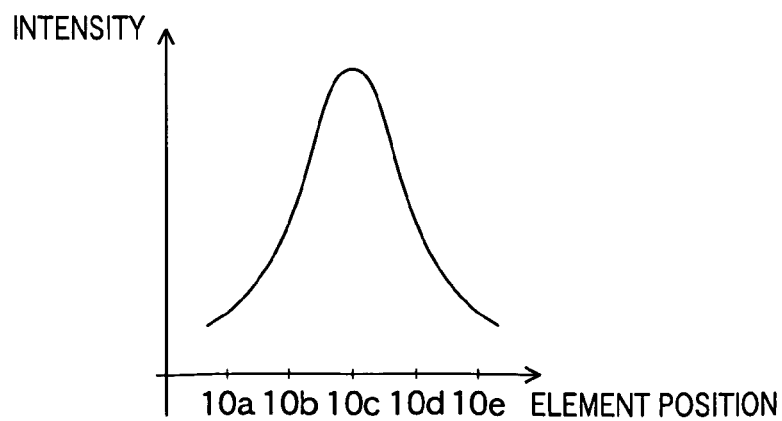

First, as shown in FIG. 2A, a case will be considered where an ultrasonic beam is transmitted toward a reflector 101 and an ultrasonic echo reflected on the surface of the reflector 101 located at depth "D" is received by using an ultrasonic transducer array including ultrasonic transducers 10a to 10e. FIG. 2B shows reception waveforms of ultrasonic echoes at the ultrasonic transducers 10a to 10e. In FIG. 2B, the horizontal axis indicates time (t) and the vertical axis indicates voltage of reception signal. Further, FIG. 2C shows an intensity distribution of the reception signals outputted from the ultrasonic transducers 10a to 10e. In FIG. 2C, the horizontal axis indicates position of ultrasonic transducer (element) and the vertical axis indicates intensity of reception signal.

The ultrasonic echoes reflected at reflection point 101a are first received by the ultrasonic transducer 10c right opposite to the reflection point 101a, and then, sequentially received by the ultrasonic transducers 10b and 10d, and the ultrasonic transducers 10a and 10e. In the case where the reflector 101 is an object that reflects the ultrasonic echoes with little scattering like a bone part, the ultrasonic echoes are received by the ultrasonic transducers 10a to 10e in an intensity distribution with the position of the ultrasonic transducer 10c as a peak thereof. As below, such a reflector (reflection surface) is called "specular reflector (specular reflection surface)".

In the case where the B-mode image is generated, a predetermined delay times are provided to the reception signals on the same phase matching line L1 and added them. Thereby, a sound ray signal SL representing ultrasonic information on a region including the reflection point 101a is formed.

Figure 3A:
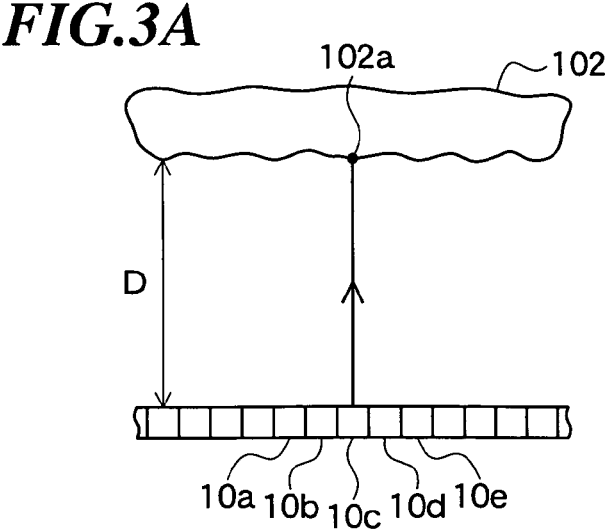
FIGS. 3A to 3C show an intensity distribution of reception signals when ultrasonic waves are transmitted toward a scattering reflector and received.
Figure 3B:
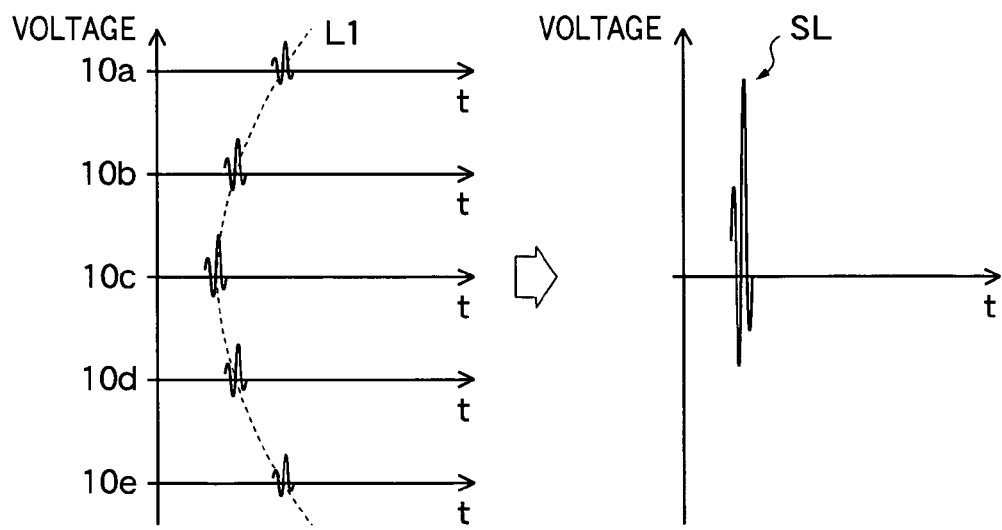

Next, the case where an ultrasonic beam is transmitted toward a reflector like a soft tissue that readily scatters ultrasonic waves will be considered. As below, such a reflector (reflection surface) is called "scattering reflector (scattering reflection surface)". As shown in FIG. 3A, when an ultrasonic beam is transmitted toward a scattering reflector 102 located at depth "D", the ultrasonic beam is scattered in various directions at reflection point 102a. Thus generated ultrasonic echoes are received by the ultrasonic transducers 10a to 10e with timing depending on the depth "D" and the position of the reflection point 102a. Since the timing is on the phase matching line L1 like the case of the reception waveform of the ultrasonic echoes shown in FIG. 2B, when phase matching is performed for generating a B-mode image, the same sound ray signal SL as shown in FIG. 2B is formed.

Figure 3C:
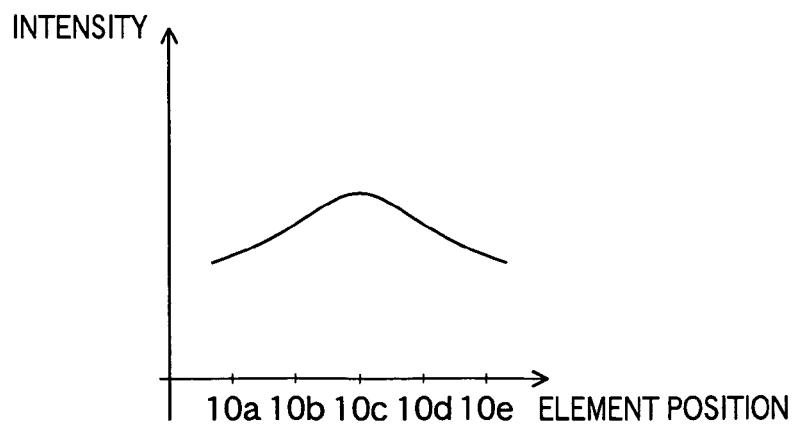

However, in the case where an ultrasonic beam is reflected by the scattering reflector, because the intensity of ultrasonic echoes is dispersed in various directions, the intensity distribution of the reception signals outputted from the ultrasonic transducers 10a to 10e becomes relatively flat as shown in FIG. 3C.

Figure 4A:
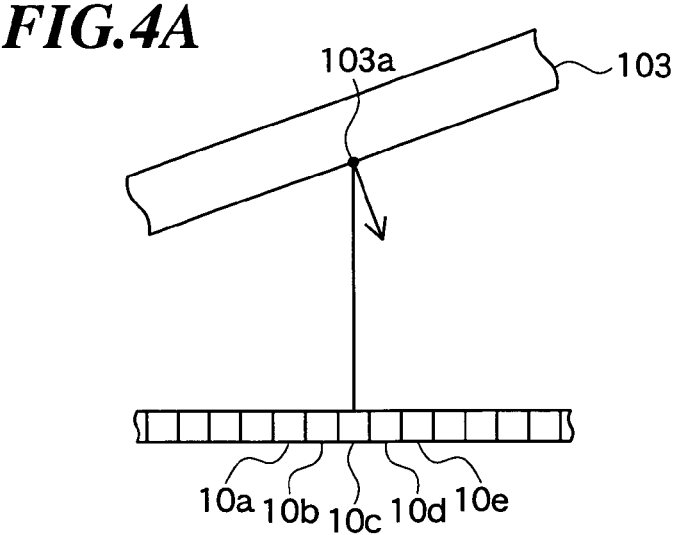
FIGS. 4A to 4C show an intensity distribution of reception signals when ultrasonic waves are transmitted toward a inclined specular reflector and received.
Figure 4B:
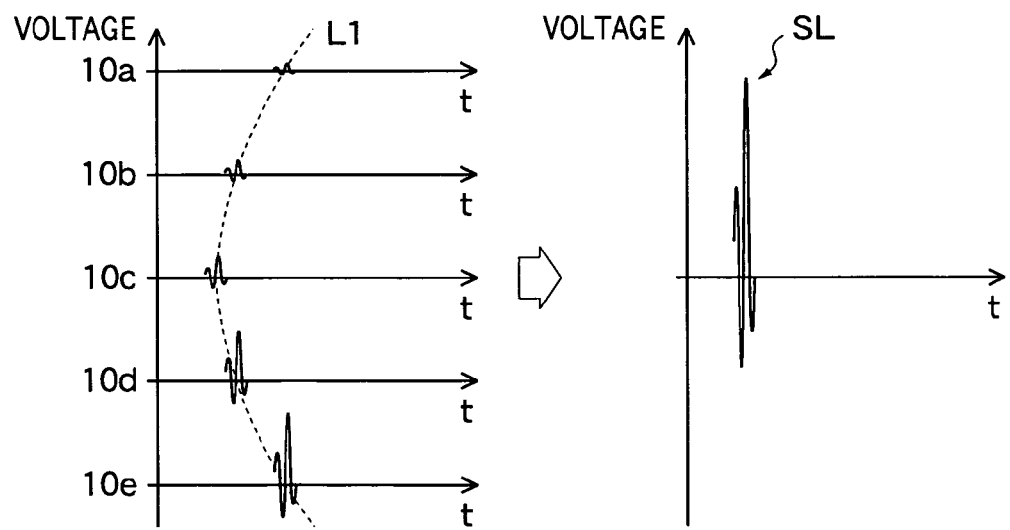

Next, the case where a specular reflector is inclined relative to the ultrasonic transducer array will be considered. As shown in FIG. 4A, when an ultrasonic beam is transmitted toward a specular reflector 103 located at depth "D", the ultrasonic beam is reflected in a direction different from the direction in which the ultrasonic beam has been transmitted according to the inclination of the specular reflector 103. Thus generated ultrasonic echoes are received by the ultrasonic transducers 10a to 10e with timing depending on the depth "D" and the position of the reflection point 103a. As shown in FIG. 4B, since the timing is on the phase matching line L1 like the case of the reception waveform of ultrasonic echoes shown in FIG. 2B, when phase matching is performed for generating a B-mode image, also the same sound ray signal SL as shown in FIG. 2B is formed.

Figure 4C:
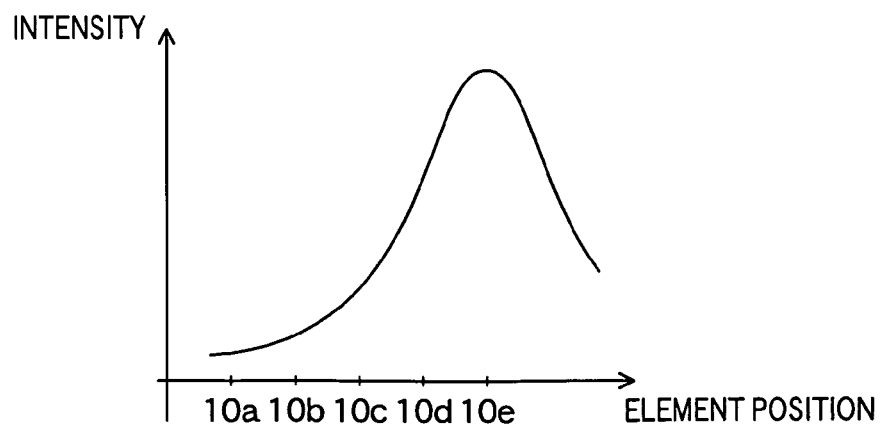

However, in the case where the ultrasonic beam is reflected by the reflector inclined relative to the ultrasonic transducer array, since the propagation direction of ultrasonic echoes is changed, the peak is shifted in the intensity distribution of the reception signals outputted from the ultrasonic transducers 10a to 10e as shown in FIG. 4C.

Thus, when phase matching is performed on the reception signals, the sound ray signals representing the reflection position of the ultrasonic echoes (the boundary between tissues) are uniformly determined, and the tissue property and inclination of the reflector can be obtained by focusing attention on the interrelationship among plural reception signals (e.g., intensity distribution). That is, it can be said that the interrelationship among plural reception signals represents qualitative information on the boundary between tissues. Especially, since the reflectance of a bone part becomes about hundred times the reflectance of a soft tissue, it is easy to analyze it at the respective reception signal levels and the hard tissue and soft tissue can be sufficiently discriminated. Further, even when a region has no indistinct outline like a part with a uniform property, the tissue property having characteristics such that the property is uniform can be obtained by focusing attention on the interrelationship among those reception signals with respect to a region in which reception signals having amplitudes not less than a predetermined value are detected.

Next, a method of imaging the tissue property based on the interrelationship among plural reception signals will be described by referring to FIG. 5.

First, the spatial intensity distribution analysis unit 26 shown in FIG. 1 obtains an intensity distribution of plural reception signals with respect to a region as a target of analysis (analysis region). That is, in a graph having the horizontal axis as position coordinate of transducer and the vertical axis as intensity of reception signal, intensity of the reception signals on the same phase matching line outputted from the plural ultrasonic transducers within aperture diameter DA of the ultrasonic transducers is plotted. Then, in the intensity distribution chart, the horizontal axis is read as data value and the vertical axis is read as frequency from a different perspective. As shown in FIG. 5, thus obtained relationship diagram is handled as a frequency distribution chart representing the relationship between random probability "x" and probability density function f(x) as below.

Figure 5:
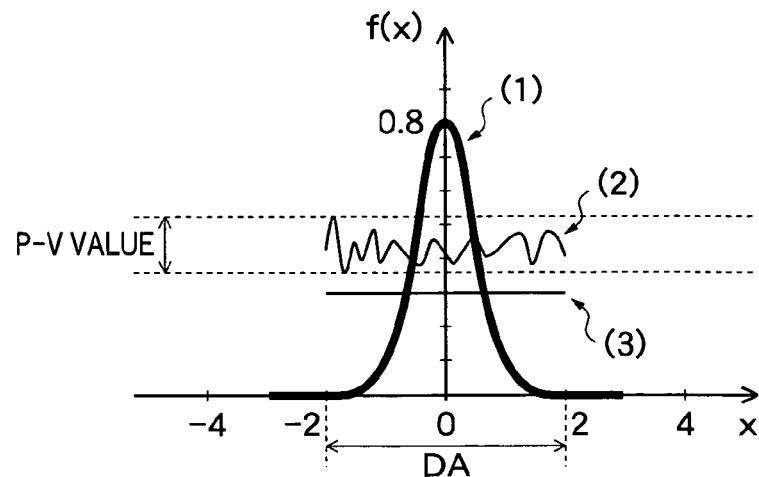
FIG. 5 shows a spatial intensity distribution of reception signals.

In FIG. 5, curve (1) represents a frequency distribution in the case where the frequency distribution is concentrated on a certain value, that is, an ultrasonic beam is reflected by a specular reflector. Further, curve (2) represents a frequency distribution in the case where the frequency is randomly distributed, that is, an ultrasonic beam is reflected by a scattering reflector. Furthermore, curve (3) shown for comparison represents a frequency distribution in the virtual case where an ultrasonic beam is reflected in plural directions with equal intensity.

The spatial intensity distribution analysis unit 26 calculates the following statistics values (1) to (5) based on the frequency distributions.

(1) Mean

A mean is used as a value representing quantitative characteristics of frequency. When an ultrasonic echo propagating from the front direction of the ultrasonic transducer array is received, the mean typically becomes zero (center), while, when a reflector is inclined relative to the ultrasonic transducer array, the mean is shifted from the center toward an end. Not only the typical arithmetic mean but also median or mode is used. Since the magnitude relationship between these arithmetic means, medians, or modes changes according to the distribution conditions of frequency, they can be used when variations in frequency are estimated.

(1-1) Median

A median refers to a value located at the center of the number of data in the case where the frequencies are arranged in order from the minimum value. When the number of data is even, the arithmetic mean of the center two values is used.

(1-2) Mode

A mode refers to a value with the highest frequency among frequencies.

(2) Variance

A variance is one of scales that indicate variations in frequency, and obtained by dividing sum of squares of deviation as differences between the respective detection data and arithmetic mean by the number of data (or the number of data−1). When the frequency distribution is close to the normal distribution and the peak rises as the curve (1), a variance value becomes smaller. Contrary, when the frequency distribution is random as the curve (2) or when the frequency distribution is uniform as the curve (3), a variance value becomes larger.

(3) Skewness

A skewness refers to a scale that indicates the degree of asymmetry around the mean of frequency, and is obtained by the following expression.

Skewness=(sum of cube of deviation)/(number of data)/(cube of standard deviation)

Zero of skewness represents that the frequency distribution is not deviated, and in this case, the arithmetic mean, the median, and the mode become equal. Further, positive skewness represents that the frequency distribution is negatively deviated, and in this case, the relationship arithmetic mean>median>mode holds. Furthermore, negative skewness represents that the frequency distribution is positively deviated, and in this case, the relationship arithmetic mean<median<mode holds.

(4) Kurtosis

A kurtosis refers to a scale that indicates degree of concentration around the mean of frequency (sharpness), and is obtained by the following expression.

Kurtosis=(sum of biquadrate of deviation)/(number of data)/(cube of standard deviation)

Here, in a standard normal distribution having a mean of "0" and variance of "1", the kurtosis becomes "3". Accordingly, the kurtosis is evaluated with numeric value "3" as a reference value. That is, when the kurtosis is "3", the frequency distribution is close to the normal distribution. Further, the smaller than "3" the kurtosis becomes, flatter the frequency distribution becomes. Furthermore, the larger than "3" the kurtosis becomes, sharper the frequency distribution around the mean becomes.

(5) P-V Value, Square Mean Between Adjacent Elements, etc.

When the frequency is randomly distributed as the curve (2), a scale indicating the degree of random is also calculated. As such a scale, for example, as shown in FIG. 5, the distance between a peak and a valley (P-V value) in the curve (2), difference square mean between adjacent ultrasonic transducers, or the like is used. These scales show that, the larger the value, the more indefinite the ultrasonic echo is and larger the speckle component is.

Figure 6:
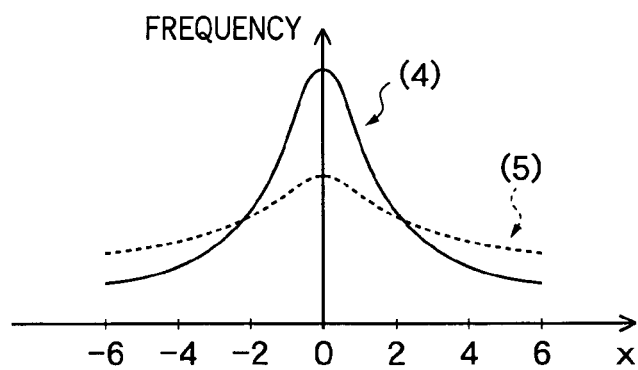
FIG. 6 is a diagram for explanation of a relationship between a spatial intensity distribution of reception signals and colors assigned to tissue property image data.
Figure 7:
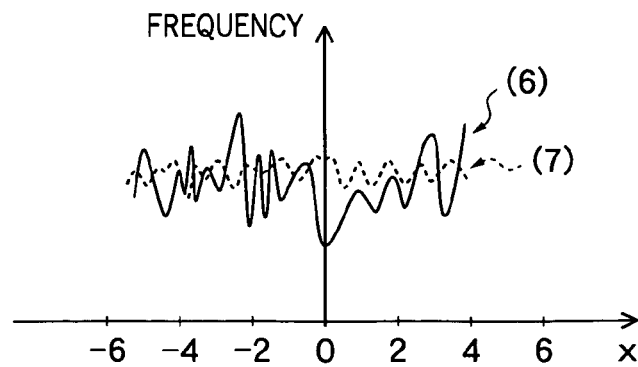
FIG. 7 is a diagram for explanation of a relationship between a spatial intensity distribution of reception signals and colors assigned to tissue property image data.

The tissue property image data generating unit 27 shown in FIG. 1 generates tissue property image data by assigning predetermined colors to display regions on the ultrasonic image corresponding to the analysis region by utilizing statistics values calculated in the spatial intensity distribution analysis unit 26 as parameters. For example, a bluish color is assigned to a region where the variance is smaller than a predetermined threshold value as shown by curve (4) in FIG. 6 (a specular reflector), and density or saturation of the colors assigned to the corresponding display regions are changed according to the values of variance and kurtosis. Further, a reddish color is assigned to a region where the variance is larger than a predetermined threshold value as shown by curve (5) in FIG. 6 (a scattering reflector). Furthermore, a yellowish color is assigned to the regions where the P-V value or square mean between adjacent elements is larger than a predetermined threshold value as shown by curve (6) in FIG. 7, (a speckle pattern or an uniform tissue within a boundary).

Figure 8:
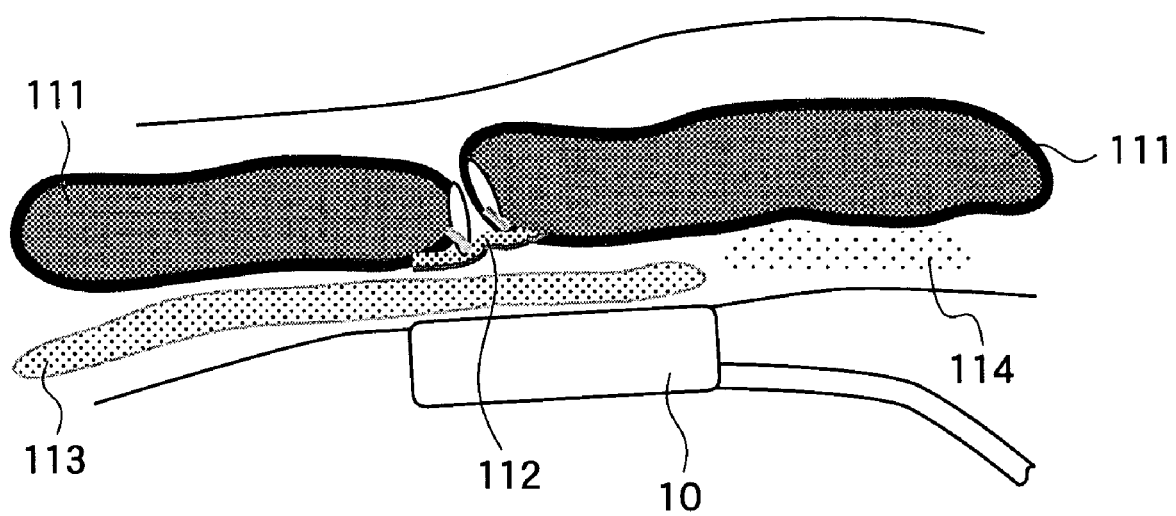
FIG. 8 is a schematic diagram showing a synthesized image of a B-mode image and a tissue property image.

FIG. 8 schematically shows a synthesized image of a B-mode image and a tissue property image. In an ultrasonic image shown in FIG. 8, surfaces of a bone part 111 and a ligament 112 are displayed in different colors according to tissue property (e.g., hardness). Further, a muscle tissue 113 and a speckle region 114 are also displayed in different colors from those of other regions. Furthermore, within the respective regions, regions having the same property (uniform tissues) are displayed in the same color.

As described above, according to the embodiment, property of tissue outlines (whether they are distinct reflection surfaces or not, hardness or softness, and so on) can be obtained based on the statistics values representing specular reflectance such as variance, and speckle patterns and property of internal tissues having no distinct reflection surface can be obtained based on statistics values representing coherency such as a P-V value. Further, thus obtained tissue property (specular reflector, scattering reflector, speckle pattern, uniform tissue, etc.) is displayed in different colors according to the tissue property, and thereby, an easily-viewable ultrasonic image in which different tissues are separated from one another can be displayed. Accordingly, especially in the periphery of the bone part or the like, even when the multiple reflection of ultrasonic waves by the bone occurs, different tissues such as tendon and muscle can be discriminated easier because the tissue property is imaged. Further, in an organ including many speckle components like a liver, the speckle pattern and the actual tissue can be clearly separated and displayed. Furthermore, even in the case where plural speckle parts having slightly different speckle patterns are adjacent, those speckle parts are distinctively displayed, and thereby, the difference of property between tissues can be displayed. Therefore, quality or efficiency of medical diagnoses can be improved using such an ultrasonic image.

In the above-mentioned embodiment, different signal preprocessings have been performed in the B-mode image data generating means 1 and the tissue property image data generating means 2. However, a common preprocessing may be performed. For example, the signal preprocessing unit 25 shown in FIG. 1 may be located before the branch to the B-mode image data generating means 1 and the tissue property image data generating means 2. In this case, such signal preprocessing may be performed before A/D conversion of reception signals or after the A/D conversion.

Further, in the embodiment, as information representing tissue property of a reflector, image data (color signals) for displaying the tissue property in different colors have been generated, however, various kinds of information can be generated other than that. For example, using an image processing technology, image data for visualizing the tissue property of a reflector according to differences in texture may be generated. Further, it is not necessarily to image tissue property of a reflector, and, for example, the information representing the tissue property of a reflector obtained based on statistics values may be made incidental to B-mode image data. Furthermore, the statistics values themselves may be used as information representing the tissue property of a reflector.

Figure 9:
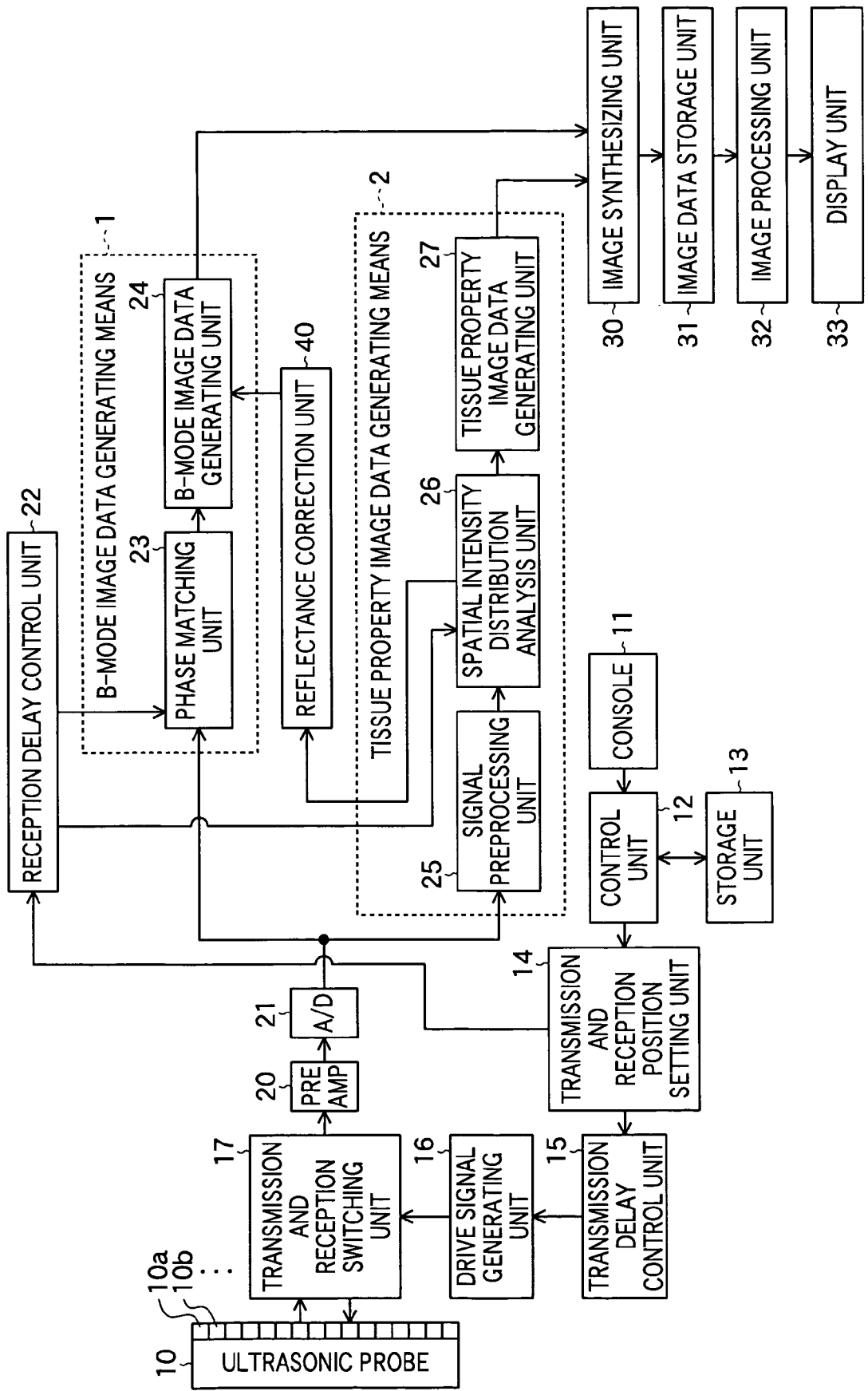
FIG. 9 is a block diagram showing a constitution of an ultrasonic imaging apparatus according to the second embodiment of the present invention.

Next, an ultrasonic imaging apparatus according to the second embodiment of the present invention will be described. FIG. 9 is a block diagram showing the constitution of the ultrasonic imaging apparatus according to the embodiment.

As shown in FIG. 9, this ultrasonic imaging apparatus further has a reflectance correction unit 40 as compared to the ultrasonic imaging apparatus shown in FIG. 1. Other constitution is the same as that of the ultrasonic imaging apparatus shown in FIG. 1.

The reflectance correction unit 40 utilizes statistics values calculated by the spatial intensity distribution analysis unit 26 as parameters to provide amounts of correction for correcting B-mode image data to the B-mode image data generating unit 24.

Here, referring FIGS. 2A and 4A again, a case will be considered where ultrasonic beams with the same intensity are transmitted to specular reflectors 101 and 103 having the same surface property. As shown in FIG. 4A, when the specular reflector 103 is inclined relative to the incident direction of the ultrasonic beam, the ultrasonic beam is reflected in a direction different from the incident direction, and the case where only part of the beam is received by the ultrasonic transducers 10a, 10b, . . . occurs. As a result, the intensity of reception signals becomes small, and thereby, despite the essentially strong specular reflector, it is only recognized as a weak diffusion distribution. Accordingly, in the embodiment, data values are corrected based on the inclination of the reflector so that B-mode image data may represent real reflectance of reflector surfaces.

The reflectance correction unit 40 has a table for reflectance correction in which amounts of correction corresponding to parameters for reflectance correction are stored, and outputs the amounts of correction corresponding to parameters on the respective analysis regions calculated by the spatial intensity distribution analysis unit 26 to the B-mode image data generating unit 24. As the parameters for reflectance correction, mode, kurtosis, or the like may be used. For example, zero of the mode represents that the reflector is not inclined as shown in FIG. 2A, and, in this case, the amount of correction of B-mode image data also becomes zero. Further, since the larger the absolute value of the mode the larger the inclination of the reflector becomes as shown in FIG. 4A, the amount of correction of B-mode image data also becomes larger.

The table for reflectance correction can be created in the following manner, for example. That is, transmission and reception of ultrasonic beams are performed from the ultrasonic probe 10 while varying the inclination of a standard reflector, and parameters (e.g., mode) are calculated thereby obtained reception signals. On the other hand, the rate of decrease in detection intensity of ultrasonic beam generated according to the inclination of the standard reflector is obtained, and the rate of decrease may be associated with parameters as an amount of correction through the inclination of the standard reflector.

Thus, according to the embodiment, B-mode image display can be performed based on the real reflectance, i.e., the accurate difference in acoustic impedance.

Further, the inclination of the reflector obtained with the parameters for reflectance correction may be used for outline correction (interpolation) in the B-mode image. Thereby, the outline continuousness can be improved, and easily-viewable ultrasonic images in which shapes of reflectors clearly appear can be generated.

Figure 10:
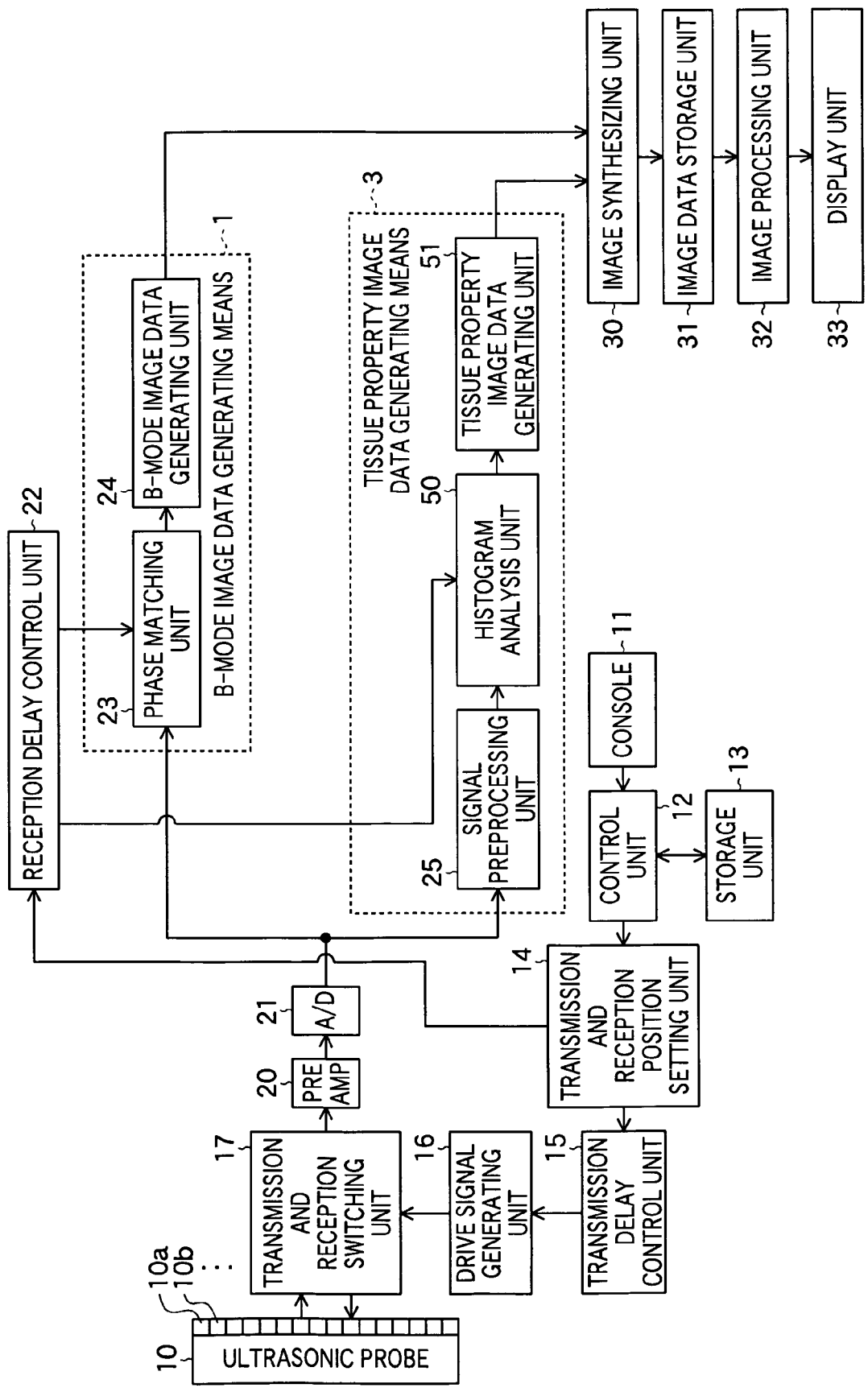
FIG. 10 is a block diagram showing a constitution of an ultrasonic imaging apparatus according to the third embodiment of the present invention.

Next, an ultrasonic imaging apparatus according to the third embodiment of the present invention will be described. FIG. 10 is a block diagram showing the constitution of the ultrasonic imaging apparatus according to the embodiment.

As shown in FIG. 10, this ultrasonic imaging apparatus has tissue property image data generating means 3 in place of the tissue property image data generating means 2 in the ultrasonic imaging apparatus shown in FIG. 1. Other constitution is the same as that of the ultrasonic imaging apparatus shown in FIG. 1.

The tissue property image data generating means 3 has a signal preprocessing unit 25, a histogram analysis unit 50, and a tissue property image data generating unit 51. The histogram analysis unit 50 generates a histogram based on plural reception signals on the same phase matching line of the plural reception signals that have been intensity corrected by the signal preprocessing unit 25, and thereby, calculates statistics values representing tissue property characteristics of a reflector. Further, the tissue property image data generating unit 51 generates tissue property image data by utilizing the calculated statistics values as parameters.

The operation of the histogram analysis unit 50 and the tissue property image data generating unit 51 will be described in detail as follows.

FIG. 11 is a flowchart showing an operation of the histogram analysis unit 50 and the tissue property image data generating unit 51 (FIG. 10) according to a first example.

Figure 12A:
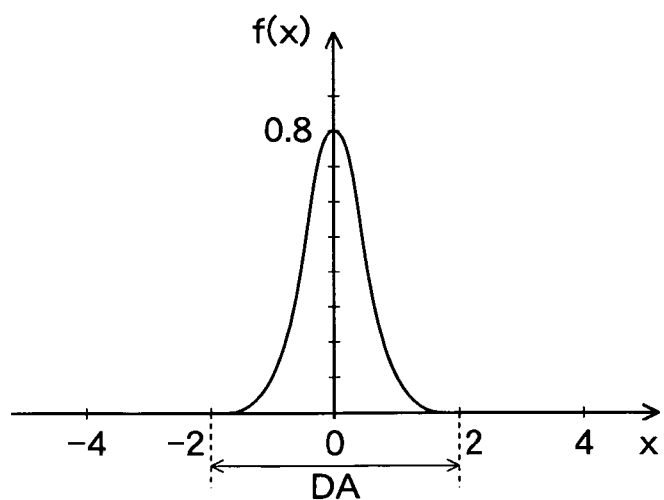
FIGS. 12A and 12B show a spatial intensity distribution of reception signals and a histogram created based thereon.
Figure 12B:
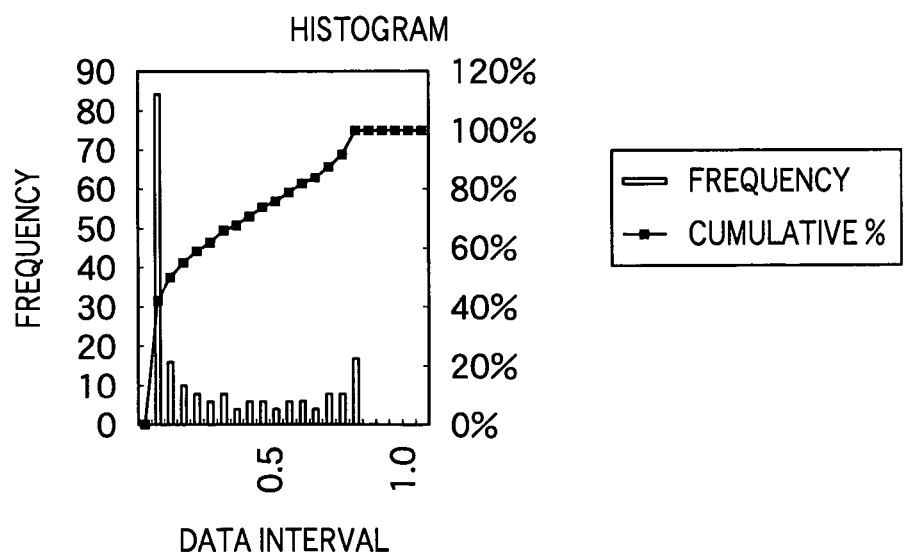

At step S11 in FIG. 11, an intensity distribution as shown in FIG. 12A is obtained with respect to reception signals on a region as a target of analysis (analysis region) on a reflector, and further, creates a histogram shown in FIG. 12B based on the intensity distribution. Here, FIG. 12A shows the intensity distribution of reception signals outputted from plural ultrasonic transducers within aperture diameter "DA" of an ultrasonic transducer array.

Then, at step S12, the created histogram is normalized so that the range of values (the horizontal axis of the histogram) may be "0" to "1".

Then, at steps S13 and S14, the distribution condition of the normalized histogram is quantified by using a beta distribution. The beta distribution is expressed as B ($\alpha,\beta$) by using shape parameters $\alpha$ and $\beta$, and probability density function f(x) in the beta distribution, r-th moment (product moment) about origin, mean E(x), variance VAR(x), and mode MOD are expressed by the following expressions (1) to (5).

$$f(x) = \frac{1}{B(\alpha,\beta)} x^{\alpha-1}(1-x)^{\beta-1} \quad (0 \leq x \leq 1) \tag{1}$$

$$\mu_r = \frac{B(\alpha+r,\beta)}{B(\alpha,\beta)} \quad (r \geq 1) \tag{2}$$

$$E(x) = \frac{\alpha}{\alpha+\beta} \tag{3}$$

$$VAR(x) = \frac{\alpha\beta}{(\alpha+\beta)^2(\alpha+\beta+1)} \tag{4}$$

$$MOD = \frac{\alpha-1}{\alpha+\beta-2} \quad (\alpha > 1, \beta > 1) \tag{5}$$

In order to obtain the beta distribution, first, at step S13, sample mean $x_{AVE}$ and variance $\sigma^2$ are obtained from the normalized histogram by using the following expressions (6) and (7).

$$x_{AVE} = \frac{1}{N}\sum_{i=1}^{n} f_i m_i \tag{6}$$

$$\sigma^2 = \frac{1}{N}\sum_{i=1}^{n} f_i m_i^2 - x_{AVE}^2 \tag{7}$$

Then, at step S14, beta distribution parameters $\alpha$ and $\beta$ are obtained by estimation according to a moment method by using the following expressions (8) and (9).

$$\alpha : x_{AVE}\left\{\left[x_{AVE}(1-x_{AVE})\Big/\left(\frac{n-1}{n}\right)\sigma^2\right]-1\right\} \tag{8}$$

$$\beta : (1-x_{AVE})\left\{\left[x_{AVE}(1-x_{AVE})\Big/\left(\frac{n-1}{n}\right)\sigma^2\right]-1\right\} \tag{9}$$

Thereby, an approximate distribution to the beta distribution is obtained.

At step S15, as shown in FIG. 13, tissue property image data is generated by classifying the beta distribution parameters and assigning predetermined colors on the display regions on the ultrasonic image corresponding to the analysis regions according to the values of $\alpha$ and $\beta$. Here, "U-shaped", "J-shaped", and "single-peaked" represent shapes of the probability density function in the beta distribution.

(i) The Case Where $\alpha<1$ and $\beta<1$

Figure 14A:
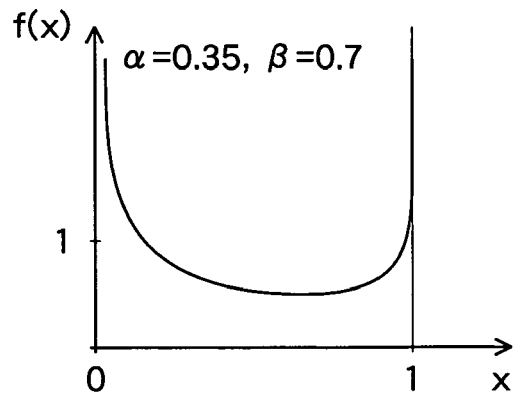
FIGS. 14A to 14C show the cases where beta distributions become U-shaped.
Figure 14B:
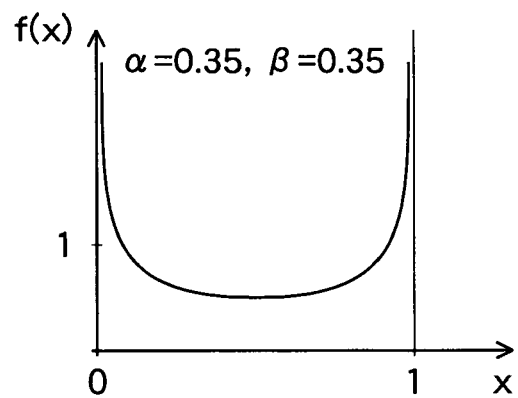
Figure 14C:
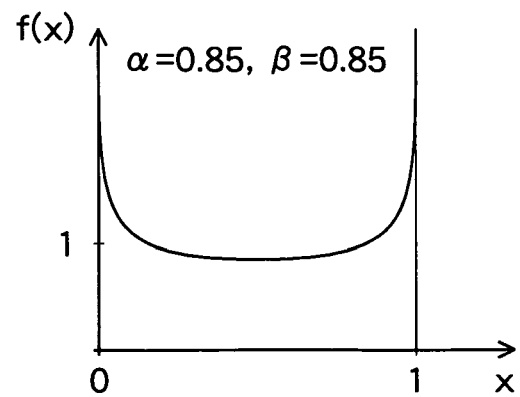

In this case, as shown in FIGS. 14A to 14C, the probability density function f(x) becomes U-shaped. The peak rises in the intensity distribution of reception signals as shown in FIG. 12A and this represents that the reflector surface is the hard tissue that specularly reflects ultrasonic waves. Accordingly, a bluish color is assigned to the tissue property image data of the display regions corresponding to the analysis region. In this regard, as shown in FIG. 14A or 14B, since the smaller the value $|\alpha\times\beta|$, the steeper the U-shaped gradient of the probability density function f(x) becomes, that represents strong specular reflection, and therefore, deep blue is assigned thereto. Contrary, as shown in FIG. 14C, since the larger the value $|\alpha\times\beta|$, the gentler the U-shaped gradient of the probability density function f(x) becomes, the specular reflection become weak, and therefore, pale blue is assigned thereto.

(ii) The Case where $(\alpha-1)\times(\beta-1)\leq 0$

Figure 15A:
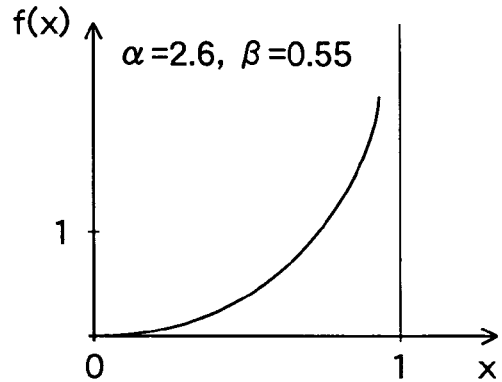
FIGS. 15A to 15D show the cases where beta distributions become J-shaped.
Figure 15B:
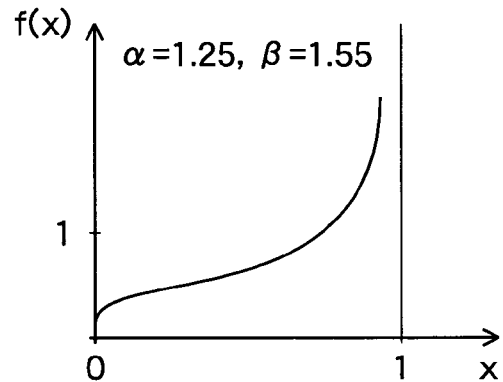
Figure 15C:
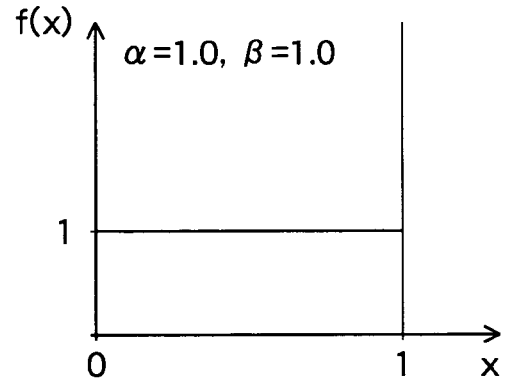
Figure 15D:
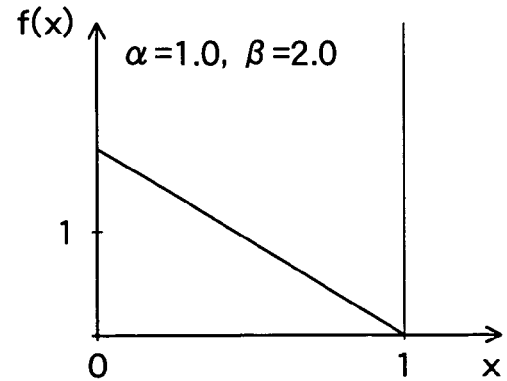
Figure 16:
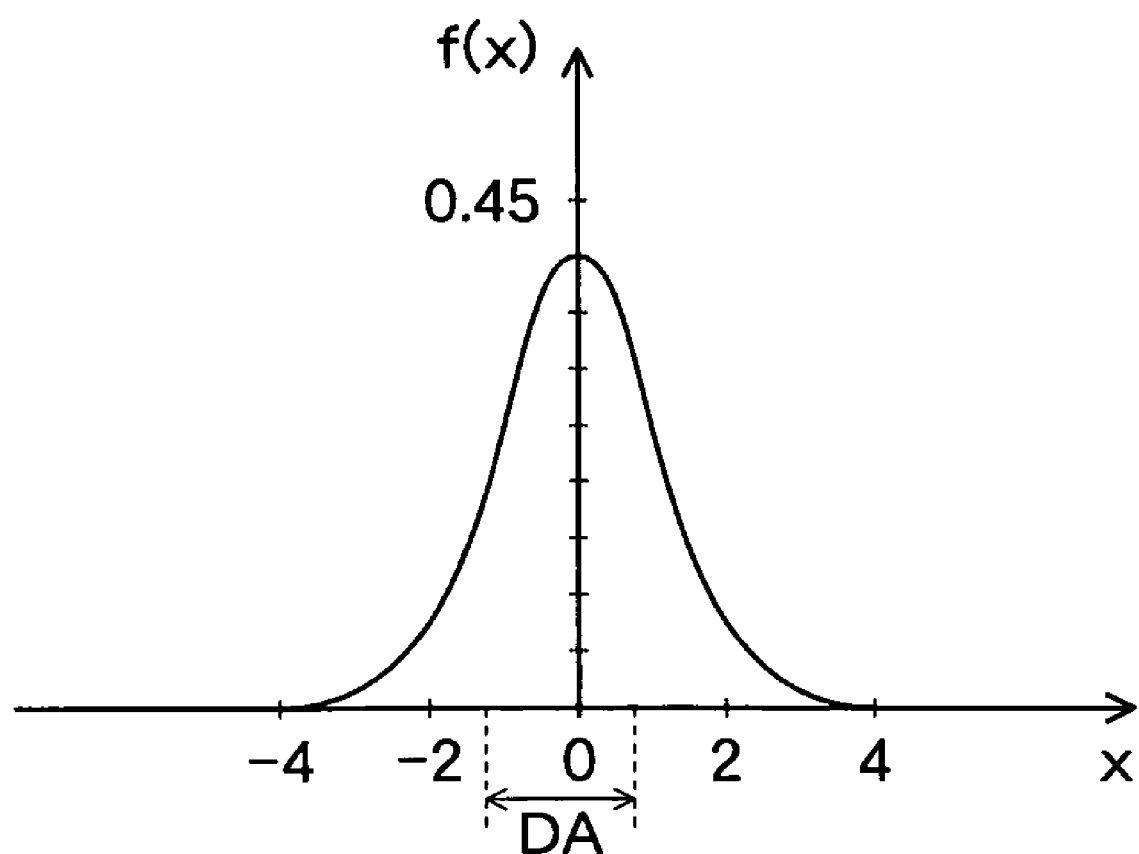
FIG. 16 shows a spatial intensity distribution in the case where a beta distribution becomes J-shaped.
Figures 17A, 17B:
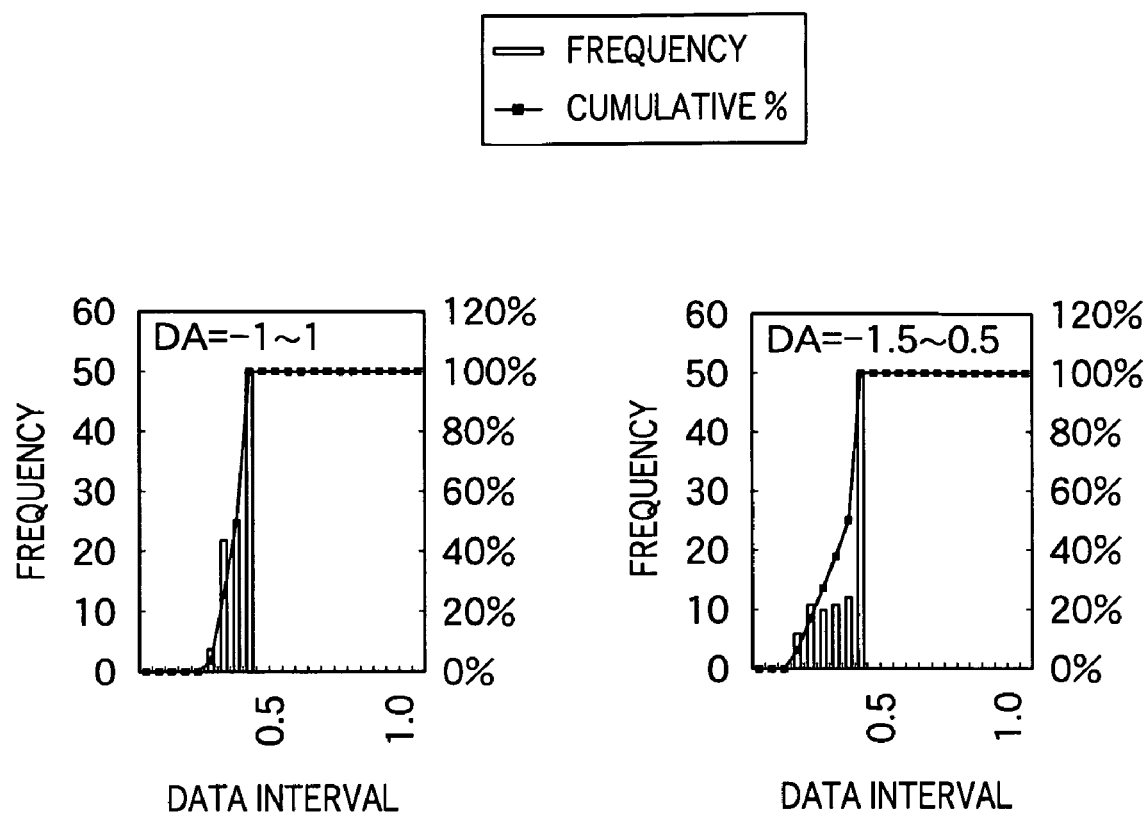
FIGS. 17A to 17D are histograms corresponding to the spatial intensity distribution shown in FIG. 16.
Figures 17C, 17D:
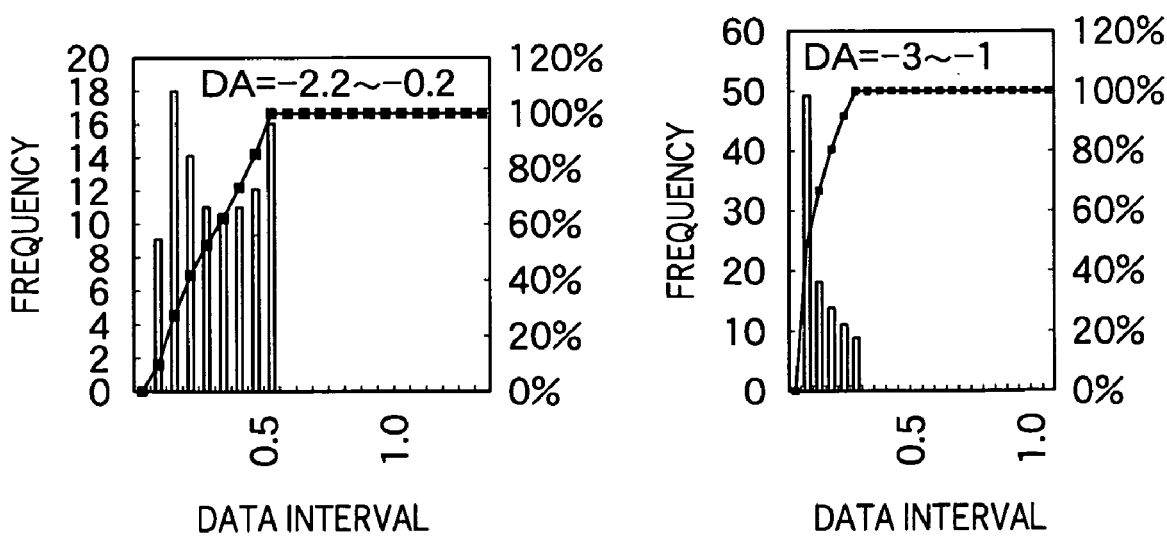

In this case, as shown in FIGS. 15A to 15D, the probability density function becomes J-shaped. The specular reflection has a peak rising to some degree in the intensity distribution of reception signals and this represents that the peak center of intensity resides outside of the aperture of the transducer array. For example, in the case where the intensity distribution shown in FIG. 16 is obtained, the histogram changes as shown in FIGS. 17A to 17D by varying the aperture diameter "DA" of the ultrasonic transducers.

In this case, a bluish color maybe assigned to the tissue property image data of the display regions corresponding to the analysis region, or a greenish color may be assigned thereto in order to discriminate the angle of the reflector from that in the above case (i). Further, as shown in FIG. 15A or 15B, the more distant from "1" the value $|\alpha/\beta|$ becomes, the steeper the gradient of the J-shape becomes, that represents strong specular reflection, and therefore, deep blue or green is assigned thereto. Contrary, as shown in FIG. 15C or 15D, the closer to "1" the value |α/β| becomes, the gentler the gradient of the J-shape becomes (e.g., gradient "0"), that represents weak specular reflection, and therefore, pale blue or green is assigned thereto.

(iii) The Case where α>1 and β>1

Figure 18A:
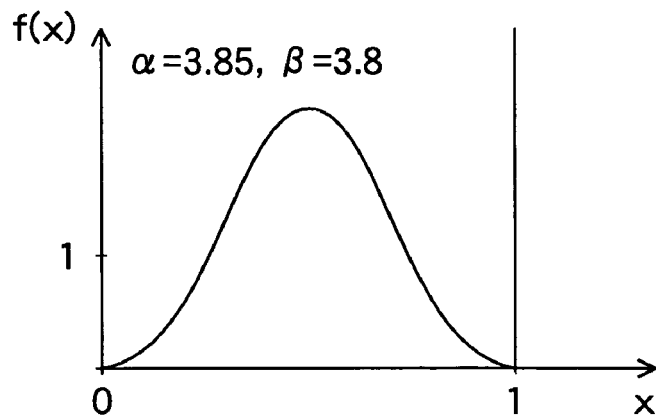
FIGS. 18A to 18C show the cases where beta distributions become single-peaked.
Figure 18B:
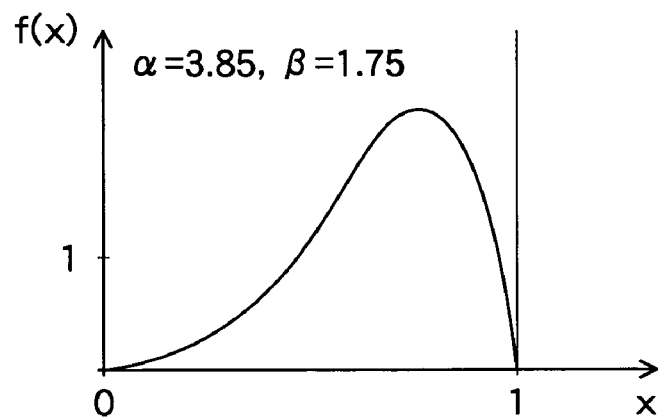
Figure 18C:
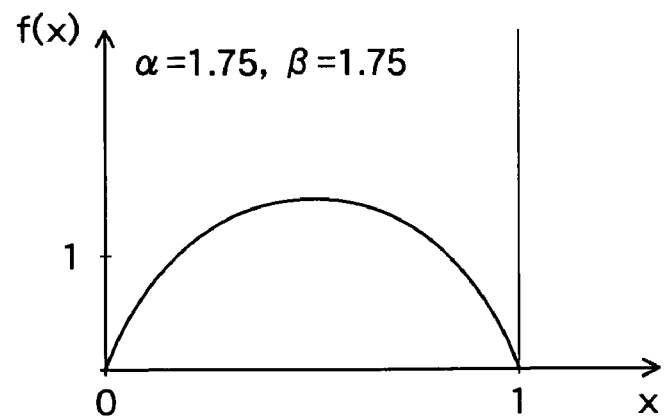

In this case, as shown in FIGS. 18A to 18C, the probability density function f(x) becomes single-peaked. That is, this represent that the intensity distribution of reception signals is a normal distribution and the reflector surface is the soft tissue that scatter reflects ultrasonic waves. Accordingly, a reddish color is assigned to the tissue property image data of the display region corresponding to the analysis region. In this regard, as shown in FIG. 18A or 18B, the larger the value |α×β| becomes, the steeper the peak of the probability density function f(x) becomes, that represents a uniform diffusion surface with small variation, and therefore, deep red is assigned thereto. Contrary, as shown in FIG. 18C, the smaller the value |α×β| becomes, the gentler the peak of the probability density function f(x) becomes, and the variation in the intensity distribution becomes greater, and therefore, pale red is assigned thereto. Alternatively, a yellowish color may be assigned to regions with values |α×β| smaller than a certain set threshold. Such regions often represent speckle components.

Next, an operation of the histogram analysis unit 50 and the tissue property image data generating unit 51 (FIG. 10) according to a second example will be explained.

In this example, in the same manner as explained in the first example, an intensity distribution with respect to reception signals on the analysis region is obtained and a histogram is created, and various statistics values are calculated based on a histogram obtained by normalizing that histogram. As the statistics values, mode, median, quartile deviation, skewness, frequency, etc. are used. Here, the quartile deviation is an indicator representing the degree of scattering of frequency, and the quartile deviation QR is obtained by the following expression by using the first quartile $X_{0.25}$ and the third quartile $X_{0.75}$. The quartile is a value in a position where the frequency is divided into quarters when data is aligned in ascending order, and the first quartile is a value located at 25% in ascending order and the third quartile is a value located at 75% in ascending order.

$$QR=(X_{0.75}-X_{0.25})/2$$

Further, other statistics values are the same as those have been described in the first embodiment.

Then, tissue property image data is generated by assigning predetermined colors to display regions on the ultrasonic image corresponding to the analysis regions based on the calculated statistics values.

(i) The Case where Variance $\sigma^2$, Quartile Deviation, or Skewness is Smaller than a Threshold Value In a condition in which frequency distribution is concentrated on the vicinity of the mean, these statistics values become smaller. In this case, the analysis region is regarded as scatter reflection surface, a reddish color is assigned to the tissue property image data of the corresponding display region. In this case, the beta distribution becomes a normal distribution (single-peaked).

(ii) The Case where Variance $\sigma^2$, Quartile Deviation, or Skewness is Larger than a Threshold Value In a condition in which the variation from the mean of the frequency distribution is large, these statistics values become larger. In this case, the analysis region is regarded as a scatter reflection surface, a bluish color is assigned to the tissue property image data of the corresponding display region. In this case, the beta distribution becomes U-shaped or J-shaped.

Here, in the above (i) and (ii), for example, as the curve (3) in FIG. 5, the respective statistics values when the frequency has a uniform distribution are used as threshold values. Further, the density or saturation of assigned colors may be changed according to the magnitude of the statistics values.

Figure 19:
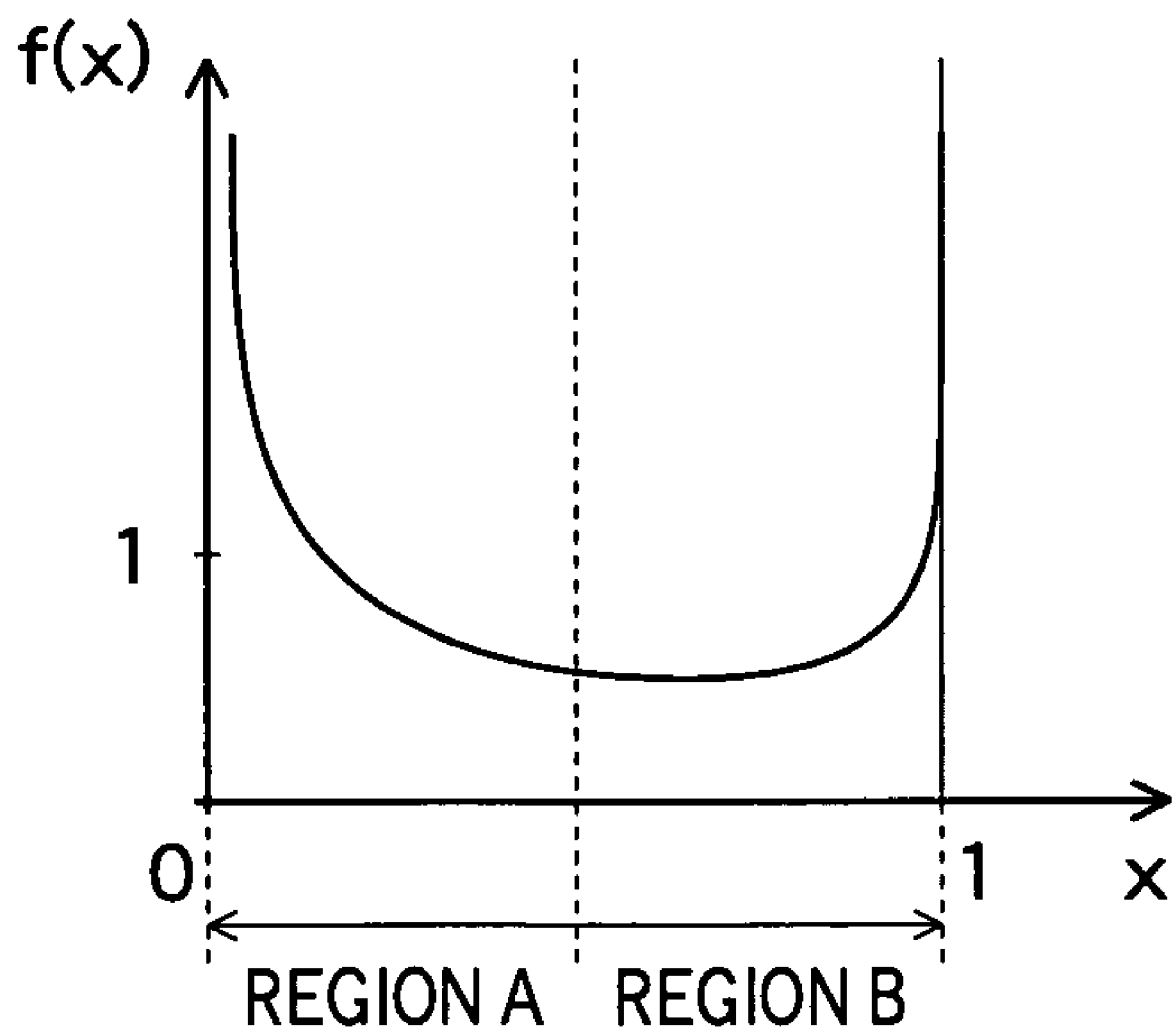
FIG. 19 is a diagram for explanation of an operation of a histogram analysis unit and a tissue property image data generating unit according to a third example.

Next, an operation of the histogram analysis unit 50 and the tissue property image data generating unit 51 (FIG. 10) according to a third example will be described. In this example, a beta distribution is obtained in the same manner as have been described in the first example, and statistics values to be used are selected according to the distribution shape thereof. That is, in the case where the shape of the beta distribution is single-peaked or J-shaped, since the analysis region can be considered as a scatter reflection surface, variance is used as a parameter. On the other hand, as shown in FIG. 19, in the case where the shape of the beta distribution is U-shaped, the data is divided into two regions A and B at the broken line in the drawing, and an average value of variances calculated with respect to the regions A and B is used as a parameter.

When the shape is recognized, pattern matching, similarity determination using the least-square method, or similarity determination to theoretical figures of statistics parameters may be performed. In this case, mode, median, rth moment about mean can be used as the statistics parameters.

Figure 20:
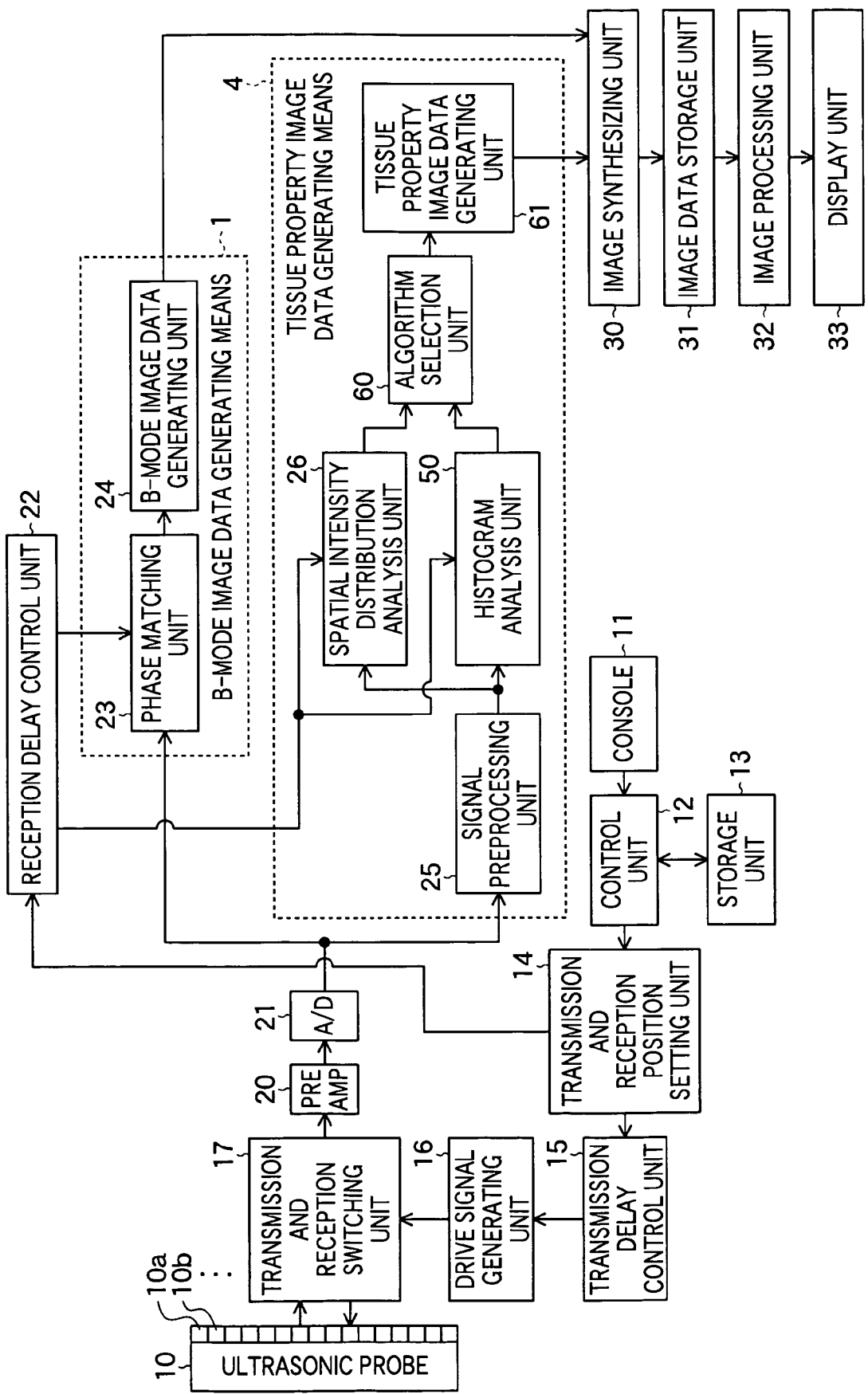
FIG. 20 is a block diagram showing a constitution of an ultrasonic imaging apparatus according to the fourth embodiment of the present invention.

Next, an ultrasonic imaging apparatus according to the fourth embodiment of the present invention will be described. FIG. 20 is a block diagram showing the constitution of the ultrasonic imaging apparatus according to the embodiment.

As shown in FIG. 20, this ultrasonic imaging apparatus has tissue property image data generating means 4 in place of the tissue property image data generating means 2 in the ultrasonic imaging apparatus shown in FIG. 1. Other constitution is the same as that of the ultrasonic imaging apparatus shown in FIG. 1.

The tissue property image data generating means 4 further has a histogram analysis unit 50, and an algorithm selection unit 60 compared to the tissue property image data generating means 2 in the ultrasonic imaging apparatus shown in FIG. 1, and a tissue property image data generating unit 61 in place of the tissue property image data generating unit 27. The operation of the histogram analysis unit 50 is the same as have been described in the third embodiment of the present invention.

The algorithm selection unit 60 provides a statistics value to be used for generating tissue property image data and an algorithm for tissue property image data generation corresponding to the kind of the statistics value from statistics values (intensity distribution information) obtained as a result from analysis in the reception control unit 26 and statistics values (histogram analysis information) obtained as a result from analysis in the histogram analysis unit 50 to the tissue property image data generating unit 61. The tissue property image data generating unit 61 generates tissue property image data by processing the statistics value using the provided algorithm. The algorithms corresponding to the kinds of the statistics values are the same as those have been described in the first to third embodiments of the present invention.

Which of the intensity distribution information and the histogram analysis information is used may be set in advance according to conditions such as the number of reception signals depending on the aperture of the ultrasonic transducer array, the intensity of transmitted ultrasonic beam, etc. Further, the use of a combination of the intensity distribution information and the histogram analysis information may be set in advance according to the kind of statistics value. For example, the histogram analysis information is used for the statistics value (variance or the like) representing a tissue property of a reflector and the intensity distribution information is used for the statistics value (kurtosis or the like) representing the inclination of the reflector. Alternatively, the statistics value to be used may be selected by the command of the operator input using the console 11. In this case, the operator may input commands while watching an ultrasonic image displayed on the display unit 33.

Thus, the use of combinations of the intensity distribution information and the histogram analysis information enables display of ultrasonic images more suitable for diagnoses.

Figure 21:
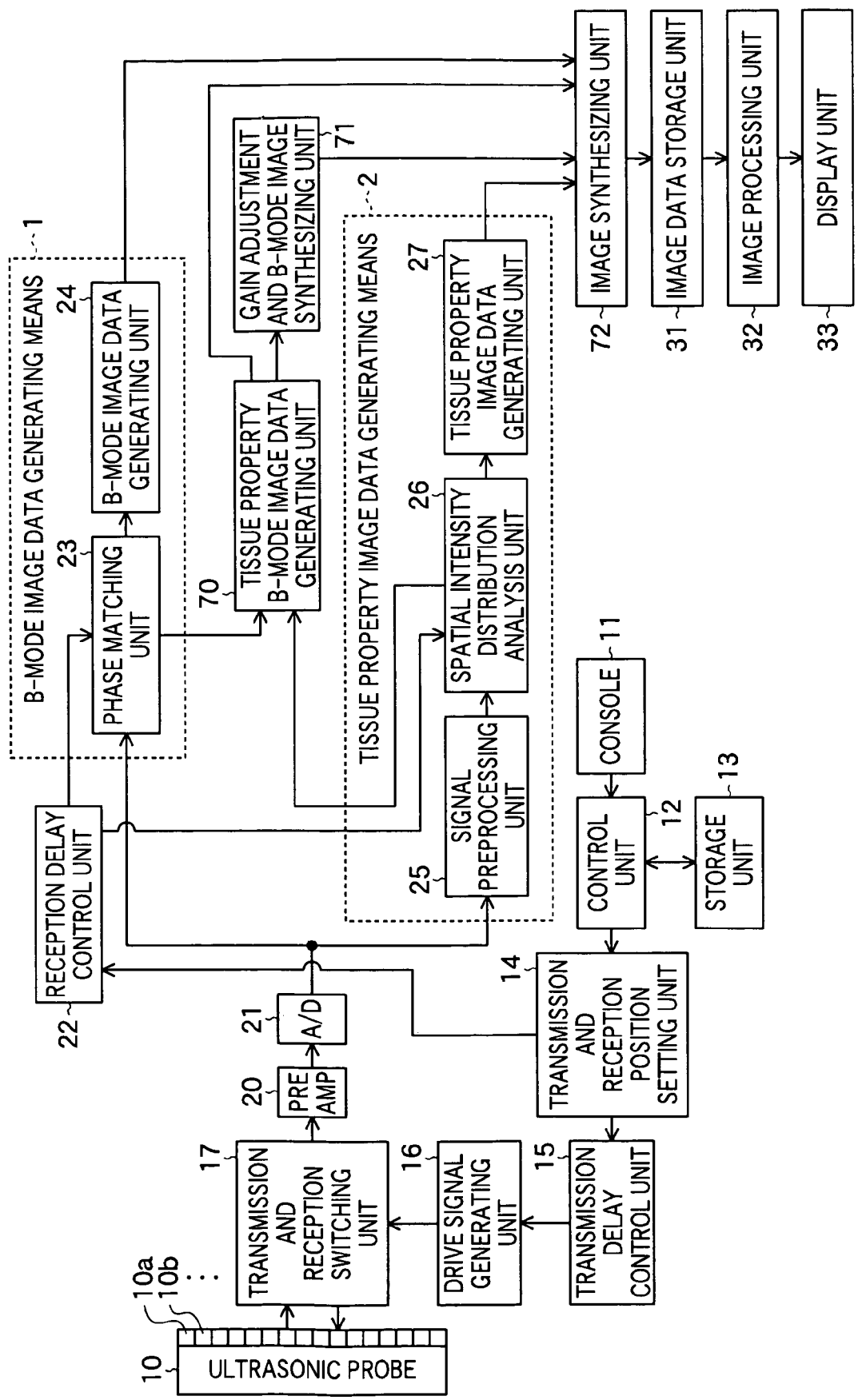
FIG. 21 is a block diagram showing a constitution of an ultrasonic imaging apparatus according to the fifth embodiment of the present invention.

Next, an ultrasonic imaging apparatus according to the fifth embodiment of the present invention will be described. FIG. 21 is a block diagram showing a constitution of the ultrasonic imaging apparatus according to the embodiment.

As shown in FIG. 21, this ultrasonic imaging apparatus further has a tissue property B-mode image data generating unit 70 and a gain adjustment and B-mode image synthesizing unit 71 in comparison with the ultrasonic imaging apparatus as shown in FIG. 1. Further, the ultrasonic imaging apparatus has an image synthesizing unit 72 in place of the image synthesizing unit 30 as shown in FIG. 1. Other constitution is the same as that of the ultrasonic imaging apparatus as shown in FIG. 1.

The tissue property B-mode image data generating unit 70 generates B-mode image data by performing envelope detection processing and STC on the sound ray data that has been formed in the phase matching unit 23, and separates B-mode image data for plural kinds of tissue property by using at least one of various statistics values calculated by the spatial intensity distribution analysis unit 26 as a parameter. Thereby, plural kinds of B-mode image data for plural kinds of tissue property are generated. For example, as described in the first embodiment, variances are calculated as statistics values and the B-mode image data is separated into regions where the variance is smaller than a predetermined threshold value (specular reflectors) and regions where the variance is larger than the predetermined threshold value (scattering reflectors). As a result, B-mode image data representing hard tissues such as bone parts and B-mode image data representing soft tissues such as muscle tissues and ligaments are generated. Alternatively, using p-v values and square means between adjacent elements as statistics values, the B-mode image data is separated into B-mode image data representing organs such as a liver and B-mode image data representing speckle pattern regions produced within. These B-mode image data by tissue property are output to the image synthesizing unit 72 directly, or via the gain adjustment and B-mode image synthesizing unit 71.

Figure 22A:
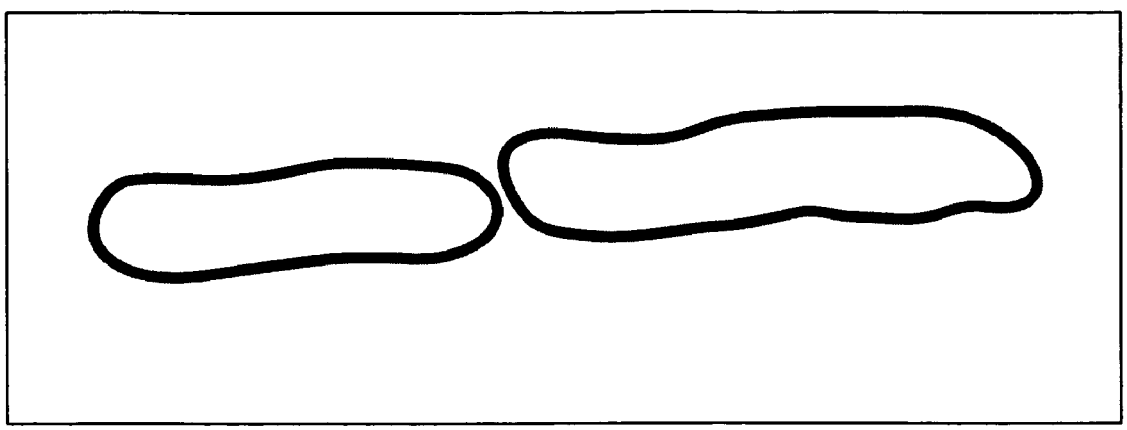
FIGS. 22A-22C are schematic diagrams showing B-mode images for plural kinds of tissue property and a synthesized image thereof.
Figure 22B:
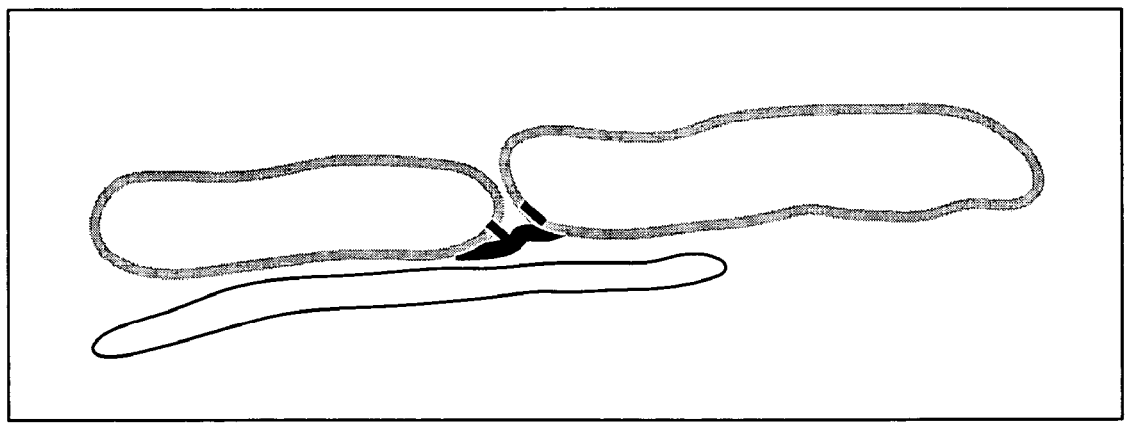
Figure 22C:
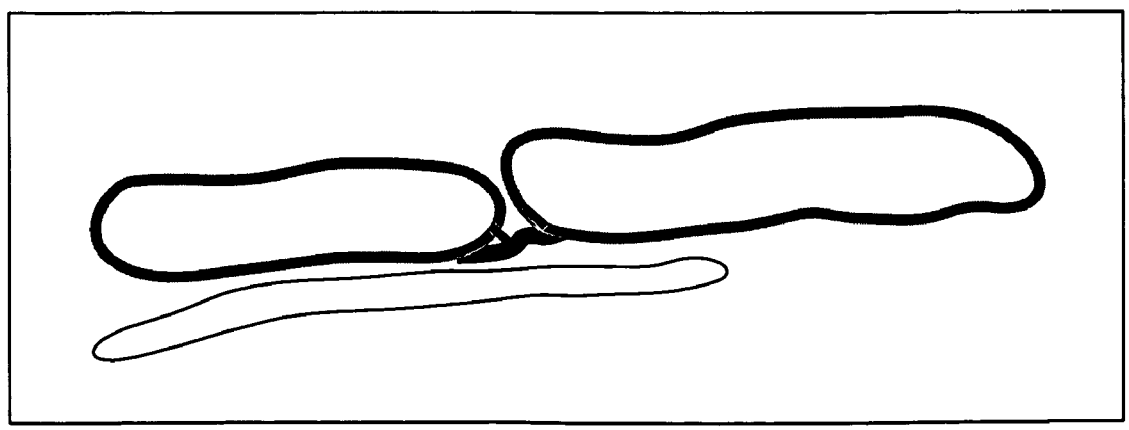

The gain adjustment and B-mode image synthesizing unit 71 generates synthesized B-mode image data by adjusting a gain with respect to each of the plural kinds of B-mode image data for plural kinds of tissue property and synthesizing them. The magnitude of gain may be set in advance according to plural kinds of tissue property or at least one statistics value to be used as a parameter, or the user may set desirable values while watching the synthesized B-mode image displayed on a screen. For example, with respect to the image in which various tissues such as bone parts, ligaments, and muscle tissues are represented (see FIG. 8), the gain of B-mode image data representing scattering reflectors is made zero, and thereby, B-mode image data extracting bone parts as shown in FIG. 22A is generated. Alternatively, the gain of B-mode image data representing specular reflectors is made lower and the gain of B-mode image data representing scattering reflectors is made higher, and thereby, B-mode image data clearly displaying the muscle tissues, ligaments, etc. as shown in FIG. 22B is generated. Thus, in the embodiment, arbitrary tissues can be emphasized in the B-mode images.

Furthermore, the gain adjustment and B-mode image synthesizing unit 71 may respectively assign predetermined color signals to the plural kinds of B-mode image data for plural kinds of tissue property. By synthesizing these, synthesized B-mode image data in which the respective tissues of bone parts, ligaments, muscle tissues, etc. can be clearly identified is generated.

The image synthesizing unit 72 generates synthesized image data based on the normal B-mode image data generated by the B-mode image generating unit 24, the tissue property image data generated by the tissue property image data generating unit 27, at least one kind of B-mode image data for at least one kind of tissue property generated in the tissue property B-mode image data generating unit 70, or the synthesized B-mode image data generated in the gain adjustment and B-mode image synthesizing unit 71. For example, in the case where a B-mode image showing a particular tissue and a tissue property image relating to the particular tissue are superimposed, the particular tissue can be displayed more easily viewable. Further, in the case where the synthesized B-mode image and the tissue property image corresponding to plural tissues shown in the synthesized B-mode image are superimposed, the respective tissues can be clearly identified.

Alternatively, the image synthesizing unit 72 may generate a screen for displaying a B-mode image for only one kind of tissue property based on the B-mode image data for one kind of tissue property outputted from the tissue property B-mode image data generating unit 70, or may generate a screen for displaying side-by-side plural B-mode images for plural kinds of tissue property, or may generate a screen for displaying side-by-side a normal B-mode image or a synthesized image distinguished in different colors with respect to plural kinds of tissue property and a B-mode image for a particular kind of tissue property.

In the fifth embodiment of the present invention, a function of generating B-mode images for plurality kinds of tissue property is added to the ultrasonic imaging apparatus as shown in FIG. 1. However, the tissue property B-mode image data generating unit 70 and the gain adjustment and B-mode image synthesizing unit 71 may be added to the ultrasonic imaging apparatuses as shown in FIG. 9, FIG. 10, or FIG. 20.

As described above, according to the first to fifth embodiments of the present invention, by using the interrelationship and property of signals such as spatial intensity distribution and statistics values of the plural reception signals, tissue property in the respective positions in the depth direction within the object can be imaged in real time by simple calculation. Further, since the tissue property image data generating means in the first to fifth embodiments of the present invention can be added as an expanded function to a general ultrasonic imaging apparatus, a system can be configured at a low price.

The invention claimed is:

1. An ultrasonic imaging apparatus comprising:
an ultrasonic probe including plural ultrasonic transducers for transmitting ultrasonic waves toward an object to be inspected and receiving ultrasonic waves reflected from the object to output plural reception signals;

B-mode image data generating means for generating B-mode image data representing a B-mode image in a region within said object based on the plural reception signals respectively outputted from said plural ultrasonic transducers; and tissue property image generating means for generating tissue property image data representing tissue property in said region by obtaining a value representing a spatial intensity distribution of at least one group of reception signals on said region from among the plural reception signals respectively outputted from said plural ultrasonic transducers and utilizing said value as a parameter, wherein said tissue property image generating means obtains a value representing a spatial intensity distribution of the at least one group of reception signals on a same phase matching line.

2. An ultrasonic imaging apparatus according to claim 1, wherein said tissue property image generating means detects the at least one group of reception signals and obtains said value based on the detected at least one group of reception signals.

3. An ultrasonic imaging apparatus according to claim 1 wherein said tissue property image generating means generates the tissue property image data by assigning a color corresponding to said parameter with respect to said region.

4. An ultrasonic imaging apparatus according to claim 3, wherein said tissue property image generating means assigns different colors to a region having a parameter representing a hard tissue and a region having a parameter representing a soft tissue.

5. An ultrasonic imaging apparatus according to claim 1, further comprising:

means for generating synthesized image data by superimposing an image represented by the tissue property image data upon the B-mode image represented by the B-mode image data.

6. An ultrasonic imaging apparatus comprising:

an ultrasonic probe including plural ultrasonic transducers for transmitting ultrasonic waves toward an object to be inspected and receiving ultrasonic waves reflected from the object to output plural reception signals;

B-mode image data generating means for generating B-mode image data representing a B-mode image in a region within said object based on the plural reception signals respectively outputted from said plural ultrasonic transducers; and tissue property image generating means for generating tissue property image data representing tissue property in said region by obtaining a value representing a spatial intensity distribution of at least one group of reception signals on said region from among the plural reception signals respectively outputted from said plural ultrasonic transducers and utilizing said value as a parameter, wherein said B-mode image data generating means generates plural kinds of B-mode image data respectively representing B-mode images for plural kinds of tissue property by performing phase matching on the plural reception signals respectively outputted from said plural ultrasonic transducers and using said value as a parameter.

7. An ultrasonic imaging apparatus according to claim 6, further comprising:

means for displaying the B-mode images for plural kinds of tissue property on a screen based on said plural kinds of B-mode image data.

8. An ultrasonic imaging apparatus according to claim 6, further comprising:

means for generating synthesized B-mode image data by adjusting a gain with respect to each of said plural kinds of B-mode image data and superimposing B-mode images for plural kinds of tissue property represented by the gain-adjusted plural kinds of B-mode image data.

9. An ultrasonic imaging apparatus according to claim 6, further comprising:

means for generating synthesized image data by superimposing a B-mode image for one kind of tissue property represented by one of said plural kinds of B-mode image data and an image based on tissue property image data representing the tissue property on a region shown in the B-mode image.

10. An ultrasonic imaging apparatus comprising:

an ultrasonic probe including plural ultrasonic transducers for transmitting ultrasonic waves toward an object to be inspected and receiving ultrasonic waves reflected from the object to output plural reception signals;

tissue property information generating means for generating information on tissue property in a region within said object based on interrelationship among at least one group of reception signals on said region from among the plural reception signals respectively outputted from said plural ultrasonic transducers;

means for generating plural kinds of B-mode image data respectively representing B-mode images for plural kinds of tissue property by performing phase matching on the plural reception signals respectively outputted from said plural ultrasonic transducers and using a value representing said interrelationship as a parameter;

means for generating synthesized B-mode image data by adjusting a gain with respect to each of said plural kinds of B-mode image data and superimposing B-mode images for plural kinds of tissue property represented by the gain-adjusted plural kinds of B-mode image data; and means for generating synthesized image data by superimposing a synthesized B-mode image represented by the synthesized B-mode image data and an image based on tissue property image data representing the tissue property on a region shown in the synthesized B-mode image.

* * * * *